US008906169B2

(12) United States Patent
Bagwell et al.

(10) Patent No.: US 8,906,169 B2
(45) Date of Patent: Dec. 9, 2014

(54) DEVICES FOR CLEARING BLOCKAGES IN IN-SITU ARTIFICIAL LUMENS

(71) Applicant: Actuated Medical, Inc., Bellefonte, PA (US)

(72) Inventors: Roger B Bagwell, Bellefonte, PA (US); Brian M Park, Bellefonte, PA (US); Maureen L Mulvihill, Bellefonte, PA (US); Gabriela Hernandez Meza, Philadelphia, PA (US); Dana B Mallen, Yardley, PA (US); Paul L Frankhouser, Miami Beach, FL (US); Josue R Crespo, Cabo Rojo, PR (US); Debora L Demers, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 0 days.

(21) Appl. No.: 14/052,917
(22) Filed: Oct. 14, 2013
(65) Prior Publication Data
US 2014/0039419 A1 Feb. 6, 2014

Related U.S. Application Data

(60) Continuation of application No. 13/571,149, filed on Aug. 9, 2012, now Pat. No. 8,574,377, which is a
(Continued)

(51) Int. Cl.
| | |
|---|---|
| *B08B 9/04* | (2006.01) |
| *B08B 1/00* | (2006.01) |
| *A61M 1/00* | (2006.01) |
| *A61B 1/018* | (2006.01) |
| *A61M 25/00* | (2006.01) |
| *B08B 9/043* | (2006.01) |
| *B08B 9/047* | (2006.01) |
| *A61J 15/00* | (2006.01) |
| *A61B 19/00* | (2006.01) |

(52) U.S. Cl.
CPC .............. *A61M 1/0078* (2013.01); *A61B 1/018* (2013.01); *A61M 25/00* (2013.01); *A61M 2025/0019* (2013.01); *A61J 15/00* (2013.01); *B08B 9/0436* (2013.01); *A61B 2019/343* (2013.01); *A61J 15/0026* (2013.01); *A61B 19/34* (2013.01)
USPC .................................. 134/166 C; 15/104.05

(58) Field of Classification Search
CPC ................. A61M 2025/0019; A61M 2209/10
USPC .......... 604/35, 43, 540, 541, 267; 134/166 R, 134/166 C
See application file for complete search history.

(56) References Cited

U.S. PATENT DOCUMENTS

| 4,979,939 A | 12/1990 | Shiber |
| 5,003,657 A * | 4/1991 | Boiteau et al. ............. 15/104.33 |

(Continued)

FOREIGN PATENT DOCUMENTS

| EP | 1 666 168 A1 | 6/2006 |
| WO | WO 2004098654 A2 | 11/2004 |
| WO | WO 2007033052 | 3/2007 |

OTHER PUBLICATIONS

International Searching Authority; International Preliminary Report on Patentability and Written Opinion of the International Searching Authority; International Application No. PCT/US2010/061900; Patent Cooperation Treaty; pp. 1-22; publisher European Patent Office; Published Geneva, Switzerland; copyright and mailing date Jun. 20, 2013; (22 pages).

(Continued)

*Primary Examiner* — Michael Kornakov
*Assistant Examiner* — Natasha Campbell
(74) *Attorney, Agent, or Firm* — Neal P Pierotti; Metz Lewis Brodman Must O'Keefe

(57) ABSTRACT

Devices and methods for the effective clearing of artificial tubes, especially in-situ clearing of artificial tubes in a living being are covered in this disclosure. An elongated clearing member includes either a fixed or an adjustable element that selectively defines the portion of the elongated clearing member that is insertable within the artificial tube. The proximal end of the clearing member is releasably secured to the driving mechanism and the driving mechanisms may comprise a wide variety of repetitive motion drivers such as voice coil motors, piezoelectric actuators, pneumatic actuators, DC motors, etc. These devices/methods may comprise a freestanding console for hands-free operation or may comprise hand-held versions. The distal working end of the clearing member may comprise tips of differing functions, including an irrigation/aspiration feature.

18 Claims, 44 Drawing Sheets

Related U.S. Application Data division of application No. 12/964,252, filed on Dec. 9, 2010, now Pat. No. 8,262,645, which is a continuation-in-part of application No. 12/274,937, filed on Nov. 20, 2008, now abandoned.

(60) Provisional application No. 60/989,484, filed on Nov. 21, 2007, provisional application No. 61/099,737, filed on Sep. 24, 2008.

(56) References Cited

U.S. PATENT DOCUMENTS

| | | | |
|---|---|---|---|
| 5,251,356 | A | 10/1993 | Oaki et al. |
| 5,279,549 | A | 1/1994 | Ranford |
| 5,897,534 | A | 4/1999 | Heim et al. |
| 5,902,314 | A | 5/1999 | Koch |
| 6,047,431 | A | 4/2000 | Canonica |
| 6,082,361 | A | 7/2000 | Morejon |
| 6,725,492 | B2 | 4/2004 | Moore et al. |
| 6,725,493 | B2 * | 4/2004 | Calabrese et al. .............. 15/110 |
| 7,918,870 | B2 | 4/2011 | Kugler et al. |
| 7,938,819 | B2 | 5/2011 | Kugler et al. |
| 8,025,655 | B2 | 9/2011 | Kugler et al. |
| 8,083,727 | B2 | 12/2011 | Kugler et al. |
| 2002/0069893 | A1 | 6/2002 | Kawazoe |
| 2002/0099387 | A1 | 7/2002 | Gauderer et al. |
| 2003/0181876 | A1 | 9/2003 | Ahn et al. |
| 2004/0181194 | A1 | 9/2004 | Perkins |
| 2005/0283095 | A1 * | 12/2005 | Nair et al. .............. 600/585 |
| 2007/0093779 | A1 | 4/2007 | Kugler et al. |
| 2007/0093780 | A1 | 4/2007 | Kugler et al. |
| 2007/0093781 | A1 | 4/2007 | Kugler et al. |
| 2007/0093782 | A1 | 4/2007 | Kugler et al. |
| 2007/0093783 | A1 | 4/2007 | Kugler et al. |
| 2007/0225615 | A1 | 9/2007 | Chechelski et al. |
| 2007/0244423 | A1 | 10/2007 | Zumeris et al. |
| 2009/0188531 | A1 | 7/2009 | Boyle et al. |
| 2009/0264833 | A1 | 10/2009 | Boyle, Jr. |
| 2011/0276079 | A1 | 11/2011 | Kugler et al. |
| 2012/0071854 | A1 | 3/2012 | Kugler et al. |
| 2012/0136382 | A1 | 5/2012 | Kugler et al. |

OTHER PUBLICATIONS

United States Patent and Trademark Office: Office Action; U.S. Appl. No. 14/182,088; filed Sep. 11, 2014; pp. 1-17; publisher United States Patent and Trademark Office; Published Alexandria, Virginal; copyright and mailing date Sep. 11, 2014; copy enclosed (17 pages).

* cited by examiner

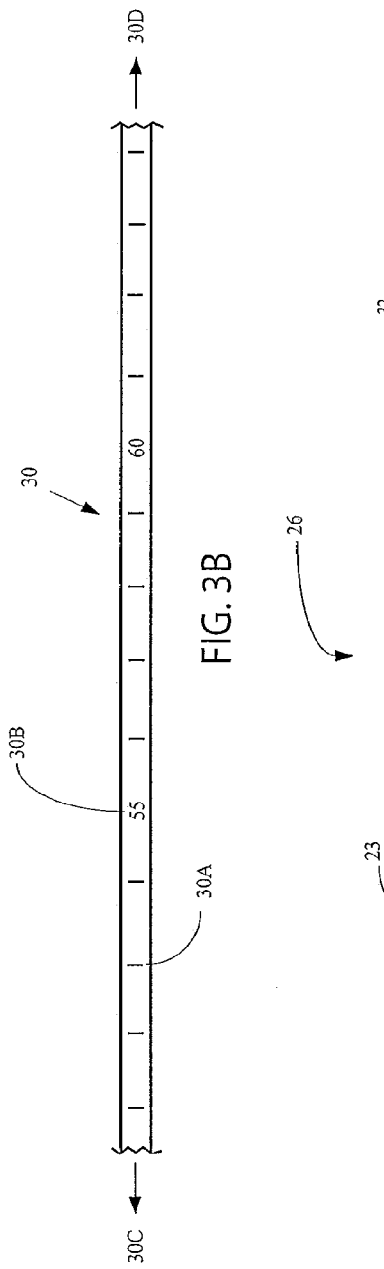
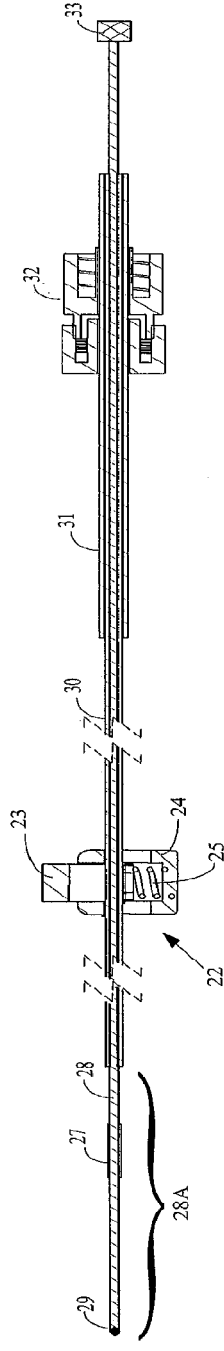
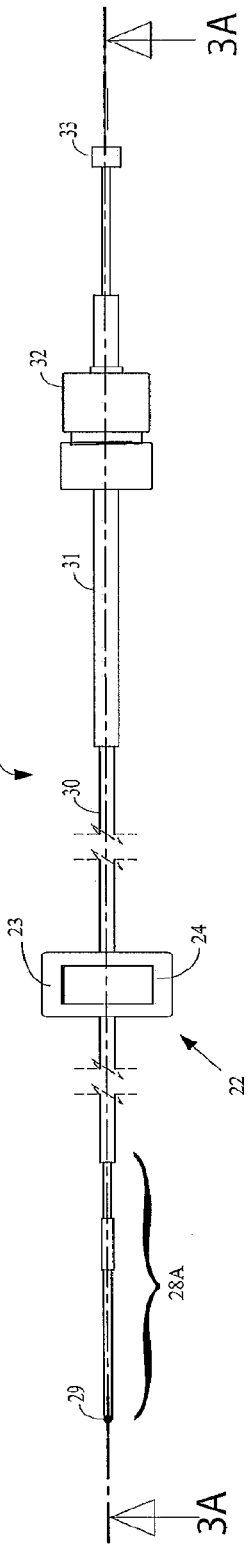
FIG. 3B
FIG. 3A
FIG. 3

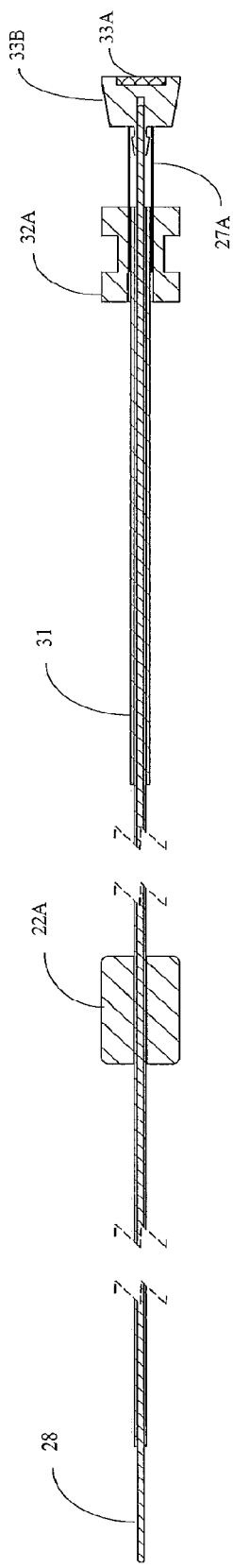
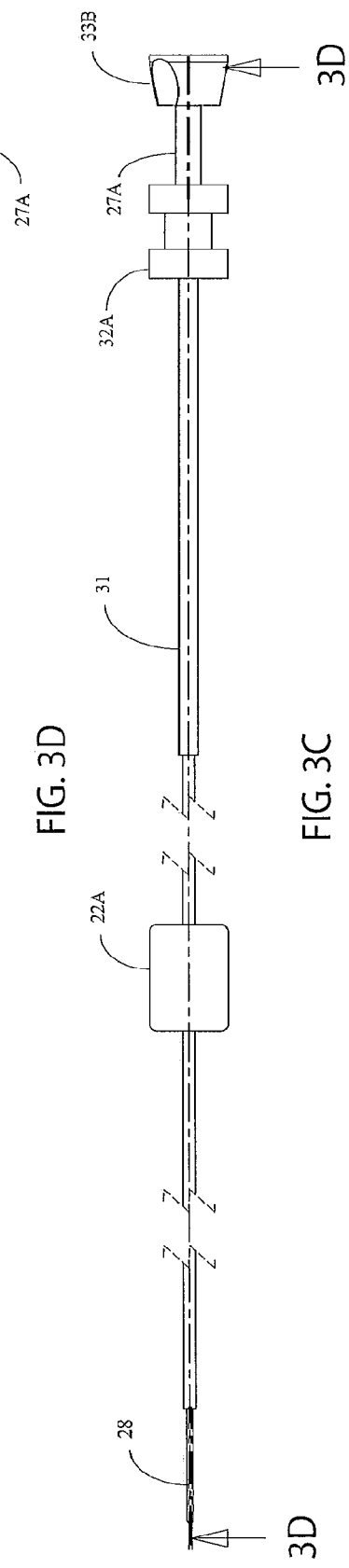
FIG. 3D
FIG. 3C

DEVICES FOR CLEARING BLOCKAGES IN IN-SITU ARTIFICIAL LUMENS

CROSS-REFERENCE TO RELATED APPLICATIONS

This continuation application claims the benefit under 35 U.S.C. §120 of U.S. application Ser. No. 13/571,149, filed on Aug. 9, 2012, entitled DEVICES FOR CLEARING BLOCKAGES IN IN-SITU ARTIFICIAL LUMENS, which in turn is a divisional application that claims the benefit under 35 U.S.C. §120 of U.S. application Ser. No. 12/964,252, filed on Dec. 9, 2010, entitled DEVICES FOR CLEARING BLOCKAGES IN IN-SITU ARTIFICIAL LUMENS and now issued as U.S. Pat. No. 8,262,645, which in turn is a continuation-in-part application that claims the benefit under 35 U.S.C. §120 of U.S. application Ser. No. 12/274,937, filed on Nov. 20, 2008 entitled FEEDING TUBE CLEANER which in turn claims the benefit under 35 U.S.C. §119(e) of U.S. Provisional Patent Application No. 60/989,484, filed on Nov. 21, 2007 entitled FEEDING TUBE CLEANER and of U.S. Provisional Patent Application No. 61/099,737, filed on Sep. 24, 2008 entitled DEVICE FOR CLEARING BLOCKAGES IN FEEDING TUBES and all of whose entire disclosures are incorporated by reference herein.

STATEMENT REGARDING FEDERALLY SPONSORED RESEARCH OR DEVELOPMENT

This invention was produced in part using funds from the Federal government under National Science Foundation Award ID nos. IIP-0810029 and IIP-0923861. Accordingly, the Federal government has certain rights in the invention.

BACKGROUND OF THE INVENTION

1. Field of Invention

The present invention generally pertains to cleaning or clearing devices and methods of using such devices for the in-situ clearing of artificial lumens within a living being including the in-situ clearing of feeding tubes.

2. Description of Related Art

The following is a description of the background of feeding tubes. It should be understood that the device and method of the present invention is not limited to the clearing of feeding tubes but is applicable to a range of artificial lumens such as indwelling catheters and that feeding tubes are being discussed simply by way of example.

A feeding tube is a medical device used to provide nutrition to patients who cannot obtain nutrition by swallowing. The state of being fed by a feeding tube is called enteral feeding or tube feeding. Placement may be temporary for the treatment of acute conditions or lifelong in the case of chronic disabilities. Varieties of feeding tubes are used in medical practice and are usually made of polyurethane or silicone.

A gastric feeding tube, or "G-tube", is a tube inserted through a small incision in the abdomen into the stomach and is used for long-term enteral nutrition. The most common type is the percutaneous endoscopic gastrostomy (PEG) tube. Feeding tubes may also be of the nasogastric type commonly called "NG-tube", which are introduced through the nose, down the esophagus and into the stomach in a procedure called Nasogastric intubation. PEG-tubes on the other hand are placed endoscopically: the patient is sedated, and an endoscope is passed through the mouth and esophagus into the stomach. The position of the endoscope can be visualized on the outside of the patient's abdomen because it contains a powerful light source. A needle is inserted through the abdomen, visualized within the stomach by the endoscope, and a suture passed through the needle is grasped by the endoscope and pulled up through the esophagus. The suture is then tied to the end of the PEG-tube that is to be external, and pulled back down through the esophagus, stomach, and out through the abdominal wall. The tube is kept within the stomach either by a balloon on its tip (which can be inflated or deflated) or by a retention dome which is wider than the tract of the tube. In the case of NG-tubes, once they are passed through the patient's nostril, a clinician must be careful not to accidentally slip the end of the tube into the patient's lungs. Additionally, upon placing the NG-tube in the patient's gastric system, for example the stomach, it is common for the tubes to slip as the primary securing means is to tape the tube to the patient immediately outside the nostril. Clinicians may pass nutrients to the patient's stomach or remove fluids from the patient via the lumen or NG-tube.

Approximately 410,000 PEG-tubes and 5 million NG-tubes are placed each year in the U.S. A down-side of the life-sustaining feeding tube is that they can become clogged. Based on a 35% clogging rate, US civilian medical facilities, treat over 1.7 million NG clogs and 140k PEG clogs annually.

Numerous conditions that may necessitate enteral nutrition over long periods of time include but are not limited to traumatic injury or elderly illness such as Alzheimer's, Parkinson's, or Cancer. When long-term enteral access is needed, gastronomy—(G), jejunostomy—(J) or gastrojejunal—(GJ) tubes are often surgically inserted. J- and GJ-tubes are employed when gastric complications are present and improved nutrient uptake is necessary. Therefore, the J-tube distal end is positioned in the bowels. Reported clogging rates of GJ and J-tubes have been as high as 35% mainly due to the small bore, considerable length, and convoluted geometries of the tubes once placed. As the discussion below suggests, standard nursing protocols to clear tube occlusions are time consuming at best and are often unsuccessful. GJ- and J-tubes are especially challenging due to the curvature associated with placement.

When a patient's enteral feeding tube becomes clogged, the process of clearing it can be time-consuming and expensive, especially if the tube must be replaced. Additionally, a clog can interrupt the patient's supply of nutrients and cause him discomfort. Many nursing policies recommend flushing feeding tubes with water every four to six 5 hours, and before and after administering medications or checking gastric residuals. Even with these policies, the rate of feeding tube occlusion is approximately 12.5%. Small-bore tubes are even more prone to clogging than are large-bore tubes, and clogging of these tubes has been shown to be a major cause of feeding downtime. A patient with an occluded tube may miss several hours of feeding and receiving nutrients before the tube is unclogged or replaced. This concern, along with patients' discomfort and the expense incurred by having to replace tubes that could not be unclogged, identifies problems to be corrected by the present invention.

Over time, feeding tubes become brittle and need to be replaced. A major cause of this is the accumulation of fungus inside the feeding tube. Standard feeding tube maintenance is to "flush" feeding tubes with water; however, this does not remove debris and fungus from the inner walls. Once a tube clogs, it is prone to reclogging.

Medications are the number one reason for tubes getting clogged. Certain medications, such as Metamucil or liquid pain reliever, build up on the inner walls of the tube and promote clogging. Other medications need to be crushed and mixed with water. If these medications are not adequately flushed or crushed finely, they will clog the tube. Older patients receive an average of 8-11 medications regularly throughout the day. Due to medical restrictions on fluid intake, or if the care-giver is rushed, an adequate flush may not occur. A clogged tube can leave an already compromised patient without medication or nutrition for hours, or even days, and is extremely frustrating to both the patient and the caregiver.

Patients with long-term feeding tubes are generally cared for at home or in a long term nursing facility. Advancements in technology and home nursing have allowed the utilization of home enteral nutrition to dramatically increase over the last few decades. While this is certainly positive, the down side is that when a feeding tube becomes clogged such that it cannot be unclogged with conventional methods, the patient must be transported to a specialty hospital to have the tube surgically removed and replaced. For persons recovering in rural areas, this could be even more problematic as an extensive car ride—several hours—may be necessary to reach the specialty hospital. This disruption is a time consuming, expensive, and agonizing experience for the patient and family members. Numerous hours without nutrients and medication could have significant adverse effects on recovery of wounded soldiers, elderly and chronically ill patients.

One product which claims the ability to assist in restoring feeding tubes by degrading the clogged matter is the CLOG ZAPPER™ available through CORPAK® MedSystems of Wheeling, Ill. and is disclosed in part in U.S. Pat. No. 5,424,299 (Monte). This product relies on a chemical solution being injected into an enteral feeding tube to clear remnant food from the tube and decontaminate the tube. The chemical solution mixture comprises maltodextrin, cellulase, alpha-amylose, potassium sorbate, papain, ascorbic acid, disodium phosphate, sodium lauryl sulfate, disodium EDTA, and citric acid. While the solution provides some assistance in degrading the clogged matter, some patients may be allergic to at least one of these ingredients and the system for introducing the chemical solution is not always successful.

The current state of science includes three approaches to remove a clog: (1) syringe flush, (2) chemical and enzymatic treatment, and (3) mechanical devices.

Syringe Flush

The most recommended approach is to use a 'flushing syringe'. The first step is to insert the syringe into the tube and pull back on the plunger to attempt to dislodge the clog. If not successful, warm water is placed into the tube and pressure, alternating with syringe suction, is performed. This may need to be repeated for up to 30 or more minutes. However, this may not always be done with enough efficiency or regularity and a high percentage of tubes remain clogged.

Chemical and Enzymatic Treatment

Chemical approaches to clog removal involve a nurse flushing the tube with a variety of reported substances, such as enzymes, meat tenderizer, soda, and fruit juices. More recently developed chemical approaches include using a dose of pancrelipase (Viokase®) and sodium bicarbonate mixed with water. The Clog Zapper uses a syringe filled with an unclogging powder with a variety of ingredients. Product directions state to allow the solution to set for an hour before flushing the tube. The InTRO-ReDUCER is a catheter that allows the solution to be introduced directly at the clog site, which has been reported to be more effective than introducing the solution at the external end of the feeding tube. Chemical approaches to clog removal are not effective. Patients can also be allergic to the ingredients in the chemical approaches, or adversely affected by the high sodium content.

Mechanical Devices

Mechanical devices to remove clogs are also available. Tiny brushes on wires can be used to break up the clog, but have been reported to pack the material in some clogs even more densely. The Enteral Feeding Tube DeClogger® by Bionix is a plastic, flexible rod with a spiral tip on the end. The DeClogger can be twisted to break through or pull out obstructions. Even when successful, these approaches can take up to 30 minutes to several hours per patient, do not leave the tube walls clear, and do not progress through tortuous paths well.

What is needed is an apparatus capable of mechanically breaking up the clogged material from the sidewalls and inner portions of indwelling artificial tubes and catheters, and especially enteral feeding tubes. In addition, a regular maintenance schedule is preferred for using the apparatus to clean the walls of the tube. This regular maintenance cleans the tube walls of debris while stopping potential nucleation sites in which new clogs can grow from.

All references cited herein are incorporated herein by reference in their entireties.

BRIEF SUMMARY OF THE INVENTION

These and other features of this invention are described in, or are apparent from, the following detailed description of various exemplary embodiments of this invention.

It is hereby noted that the term "in situ" is defined as performing an act on an element while the element is being utilized for its commonly known function. For example, performing the act of clearing a clog or blockage from a feeding tube in situ refers to cleaning or clearing a clog or blockage in a feeding tube while the feeding tube is connected to the digestive system of a being, human or other.

It should be understood that it is the Applicant's belief that where the clearing member of the embodiments disclosed herein utilizes a brush or brush function along any portion of the clearing member that makes any entry into the artificial lumen, the clearing member also cleans that interior portion of the artificial lumen.

A device is disclosed for the in situ clearing of blockages in artificial tubes (e.g., feeding tubes, including pediatric feeding tubes, PEG-tubes, NG-tubes, GJ-tubes, NJ-tubes, etc.) completely or partially disposed within a living being. The device comprises: a controller that remains outside of the living being, and wherein the controller comprises an actuator (e.g., voice coil motor; DC motor; piezoelectric actuator such as amplified piezoelectric actuators and Langevin transducers; solenoid motor; pneumatic motor, etc.) for generating repetitive motion (e.g., reciprocating, rotating, etc.); a clearing member having a first end that is releasably coupled to the actuator and having a second working end that is insertable into an opening in the artificial tube; wherein the second working end has a portion that comes into repetitive contact with a blockage in the artificial tube for clearing the blockage therein, wherein the clearing member comprises a flexible material that permits the clearing member to make repetitive contact with the blockage while the clearing member is positioned within a straight portion or within a curved portion of the artificial tube.

A method is also disclosed for the in situ clearing of blockages in artificial tubes (e.g., feeding tubes, including pediatric feeding tubes, PEG-tubes, NG-tubes, GJ-tubes, NJ-tubes, etc.) completely or partially disposed within a living being. The method comprises: 10 coupling a first end of a releasably-securable flexible clearing member to a controller and wherein the controller remains outside of the living being; inserting a second working end of the flexible clearing member into an opening in the artificial tube; energizing the controller such that the flexible clearing member experiences repetitive motion (e.g., reciprocating, rotating, etc.) and positioning the flexible clearing member such that the second working end 15 of the flexible clearing member comes into repetitive contact with the blockage for clearing the blockage therein; and wherein the flexible clearing member clears the blockage when positioned within a straight portion or within a curved portion of the artificial tube.

BRIEF DESCRIPTION OF SEVERAL VIEWS OF THE DRAWINGS

Exemplary embodiments of this invention will be described with reference to the accompanying figures.

FIG. 3 is a side view of the clearing stem of the present invention;

FIG. 3A is a cross-sectional view of the clearing stem taken along line 3A-3A of FIG. 3;

FIG. 3B is a partial view of the sheath depicting both integer and periodic length markings;

FIG. 3C is a side view of an alternate clearing stem that is the preferred embodiment of the present invention;

FIG. 3D is a cross-sectional view of the alternate clearing stem of FIG. 3C taken along line 3D-3D of FIG. 3C;

DETAILED DESCRIPTION OF THE INVENTION

Figure 1:
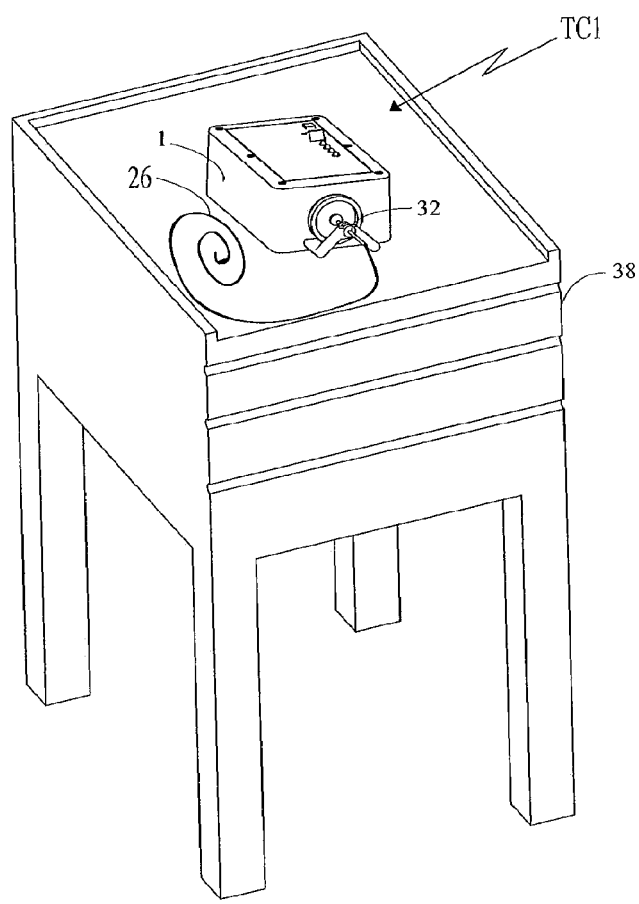
FIG. 1 is an isometric view of the control box and clearing stem of the present invention resting on a table.
Figure 1A:
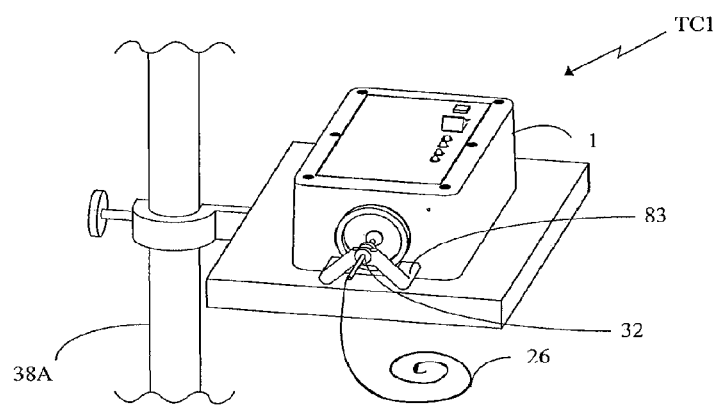
FIG. 1A is an isometric view of the control box and clearing stem of the present invention disposed on another device support (e.g., a pole cart, bed, etc.), shown in partial, adjacent the patient.

The preferred embodiments of this present invention are illustrated in FIGS. 1-29E with the numerals referring to like and corresponding parts.

The present inventions are portable devices, as well as methods for such devices, for effectively removing, moving or breaking up a clog from the internal portions of an artificial tube or catheter, enteral tube, and preferably a feeding tube, including pediatric feeding tubes. The action of removing clogs and clearing artificial tubes can also be referred to as a "maintenance action".

As will be discussed in detail later, there are basically two types of tube clearers (TC) disclosed herein, both of which are mechanical tube clearers. The first type of tube clearer TCI includes several embodiments that generate reciprocating motion of a clearing member for removing, moving or otherwise breaking up a clog in the artificial tube. This tube clearer TCI is preferred for use in nastrogastic (NG) feeding tubes, although it should be understood that TCI is not limited for only clearing NG feeding tubes. FIGS. 1-17B, 29, 29B, 29C, 29D and 29E are directed to TCI.

The second type of tube clearer TC2 involves the generation of rotational motion of a clearing member for removing, moving or otherwise breaking up a clog. This tube clearer TC2 is preferred for use in percutaneous endoscopic gastric (PEG) feeding tubes, although it should be understood that TC2 is not limited for only dealing PEG feeding tubes. FIGS. 5A, 5D, 18A-28, and 29A-29D are directed to TC2.

Both types of tube clearers TCI and TC2 are unique to feeding tube clearing and overcome major obstacles in critical and long-term care medicine by clearing clogged feeding tubes quickly and efficiently. As will be discussed in detail later, the tube clearer TCI and TC2 can remove a clog much faster (e.g., in less than 6 minutes) and at a much greater success rate than other currently-available clearing methodologies/devices, while at the same time, resulting in cleaner tube walls. Existing methodologies/devices simply do not work at all, do not clear the clogs properly, or they take a considerable time to do so.

In both tube clearers TCI and TC2, an activation unit or controller remains external to the artificial tube and therefore the patient. The activation unit or controller delivers energy to a clearing stem (also referred to as a "clearing member") which is inserted into the artificial tube and whereby the clearing stem destroys the clog (e.g., clogs of food and/or ground medication, etc.) and cleans the tube walls. As a result, the activation units in these clearers TCI and TC2 are reusable devices and the clearing stems are disposable. The clearing stems of TCI and TC2 operate in narrow tube diameters, through several radial curves sufficient to reach, e.g., the bowel. Thus, the tube clearers TCI and TC2 clear safely and with greater efficiency for NG-, PEG-, GJ- and NJ-tubes. Both tube clearers TCI and TC2 require no complicated set up, e.g., no tuning is required.

Reciprocating Tube Clearer TCI

As shown in FIG. 1, the tube clearer TCI comprises an activation unit (also referred to as the "control box" or "controller") 1 which remains external to the artificial tube 39 (see FIG. 4) being cleared, and therefore is also external to the patient (not shown). The activation unit 1 delivers energy to a clearing stem 26 which clears as it moves through the tube inner lumen 41 of the indwelling artificial tube 39, destroying the clog 40 and clearing the walls of the artificial tube 39, viz., the tube inner lumen 41 walls. Where feeding tubes are being cleared by the tube clearer TCI, the tube clearer TCI breaks up clogs of food and ground medication in a short time (e.g., less than 6 minutes). The reusable control box 1 includes a motor which drives (actuates) the disposable clearing stem 26. The control box 1 is positioned and releasably secured onto a table, tray, or nursing cart 38, such as shown in FIG. 1. Alternatively, the control box 1 can be positioned on a pole cart 38A (see FIG. IA), or bed rail or any other type of support that is adjacent, or which can be moved adjacent to the patient or living being.

As shown most clearly by way of example in FIG. 3A, the clearing stem 26 comprises a wire 28 running concentrically through a sheath 30. The wire 28 protrudes from the end of the sheath 30 and is actuated while the sheath 30 remains stationary and is secured to a non-moving portion of the control box 1. The motion at the wire tip 29 clears the occlusion or clog 40.

Control Box 1

Figure 2A:
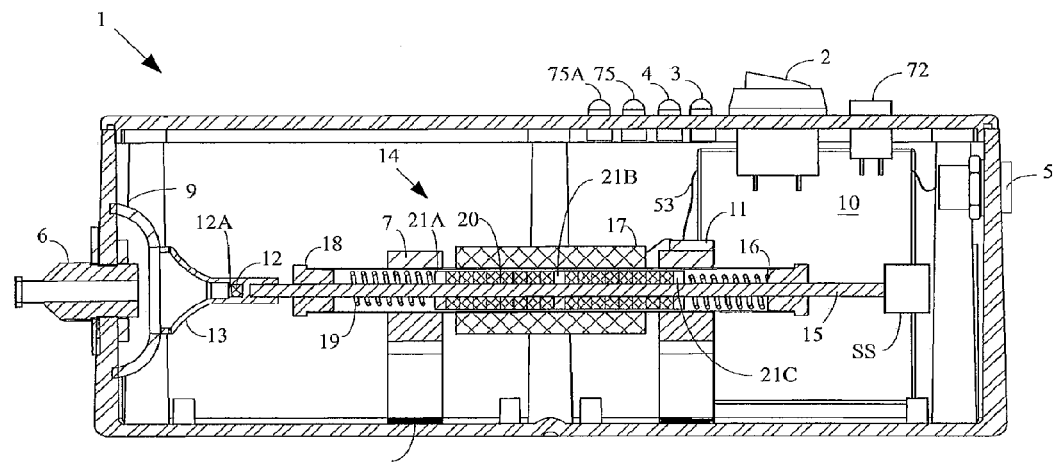
FIG. 2A is a cross-sectional view of the control box taken along line 2A-2A of FIG. 2.
Figure 2:
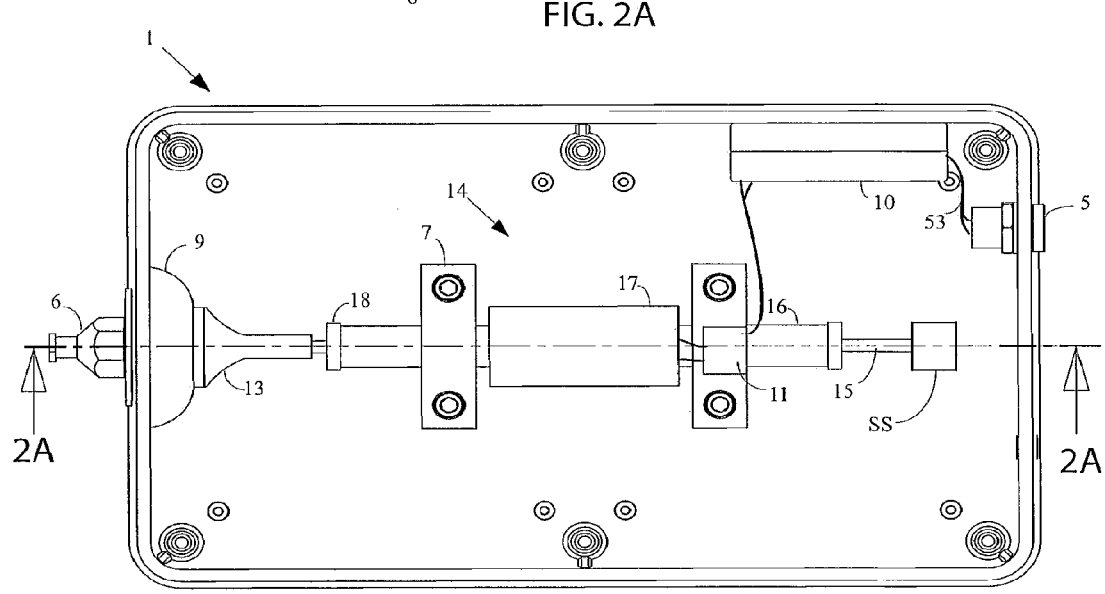
FIG. 2 is a top plan view of another control box with the lid removed.
Figure 2B:
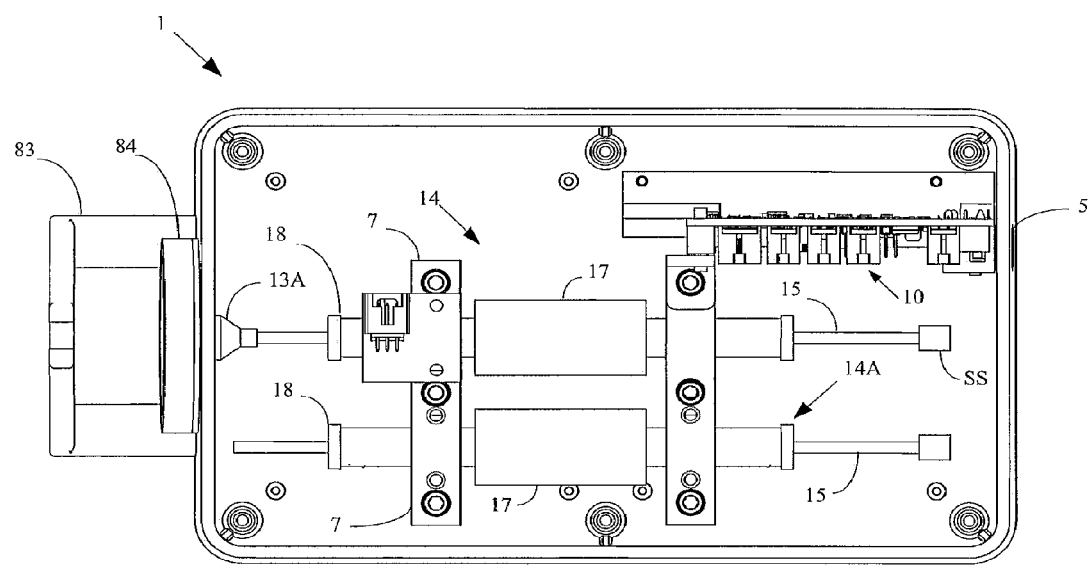
FIG. 2B is a top plan view of an alternate embodiment of the control box of FIGS. 1 and 1A with the lid removed.

As shown in FIGS. 2-2B, the control box 1 comprises a motor 14, drive electronics 10, electrical connectors, wiring, and clearing stem connectors. The control box 1 is preferably constructed of polymer, although metallic, rubber, or a combination of all three materials may be used. The preferred polymer is flame-retardant ABS plastic, although other polymers such as polyurethane, polypropylene, and nylon, but not limited to such, may be used for, among other things, their lightweight composition and structural integrity. Metals such as aluminum, titanium, steel, brass in sheet or machined form may also be used, especially where certain motor technologies (e.g., amplified piezoelectric actuators (APAs)) are used; to maintain efficiency of APAs, the non-moving portion of them needs to be effectively clamped or else too much deflection on the side that should be clamped will greatly reduce the APAs' efficiency; a metal control box provides sufficient rigidity to properly clamp. The control box 1 has a releasable securing mechanism such as rubber feet, mechanically actuated suction cup, screws, rubber stops, or magnetic feet, etc.

that facilitates its use on a table or nursing cart. As such, the control box 1 remains portable but is stationary during use. The motor 14 drives a motor shaft 15 that generates the reciprocating motion. It should be understood that FIG. 2B depicts the preferred control box 1 because it comprises a novel clearing stem-control box interface, as will be discussed in detail later with regard to FIGS. 16B-16C. FIG. 2B also depicts, by way of example only, the use of a counter balance mechanism 14A to counteract vibration caused by the reciprocation of an actuating motor 14, as will also be discussed later.

In another embodiment, the electronic circuit and componentry for example power indicator 3, fault indicator 4, enable switch 72 can be incorporated into a membrane switch such as XYMOX Technologies, Inc. Model No. 54894.

Clearing Stem/Member and Connectors

The clearing stem 26 comprises a sheath 30 which is fed into the clogged artificial tube. The preferred sheath material is polytetrafluoroethylene (PTFE) although other tube materials may also be used such as, but not limited to, nylon, polyvinyl chloride (PVC), polyurethane, polyethylene, polypropylene, fluoropolymer, Viton, Hytrel. As mentioned previously, within the sheath 30 is a wire 28, which is attached to the motor 14. The motor 14 supplies reciprocating (also referred to as "oscillating") motion to the wire 28, causing the wire 28 and its wire tip 29 to reciprocate back and forth. As can be seen most clearly in FIGS. 3-3A, the wire 28 protrudes beyond the end of the sheath 30, and into the clog 40 (FIG. 4) which causes the disruption of the clog 40. The length of the wire protrusion 28A beyond the end of the sheath 30 strongly impacts the effectiveness of the clearing. In addition, the roundness of the wire tip 29 strongly impacts the ease of insertion of the clearing stem 26 into the artificial tube 39.

The clearing stem 26 may comprise a length of 60 cm to 250 cm, but preferably 180-220 cm, and most preferably, 203 cm. In addition, the wire 28 may comprise a flexible wire most preferably stainless steel twisted wire, but could also be helical wrapped wire or a flexible stainless steel wire encased in a polymer wrapping, such as shrink wrap. The wire 28 protrudes from the end of the sheath a distance of 0 to 13 cm, but preferably 1 to 5 cm and most preferably 2.54 cm. The clearing stem 26 releasably secures to the control box 1 via a Luer clearing stem connector 6.

It should be noted that, alternatively, the wire 28 may be hollow to enable other features such as irrigation or aspiration of the artificial lumen, as will be discussed later.

Figure 4:
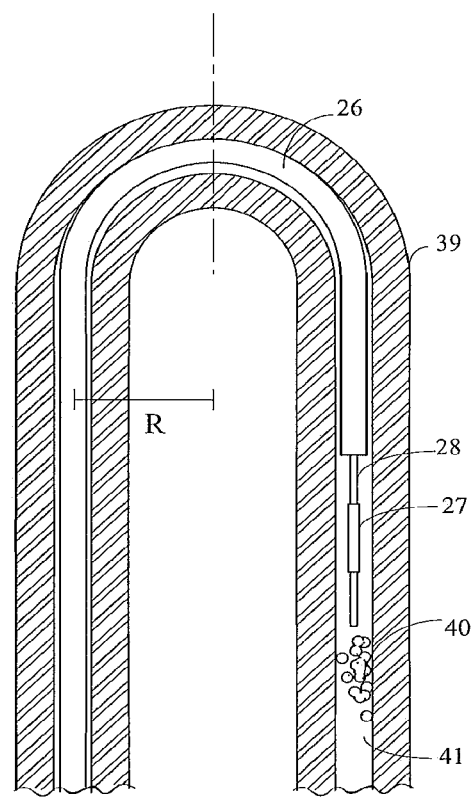
FIG. 4 is top plan view shown in cross-section depicting the clearing stem inserted within an artificial lumen in a living being showing the clearing stem clearing a blockage and depicting the stem's radius of curvature.

FIGS. 3-3A depict the clearing stem 26 which uses a magnetic-based and Luer lock connection to the control box motor 14, a stem stiffener 31 at a proximal end of the clearing stem 26, the amount that the wire tip 29 extends beyond the sheath 30 (referred to as the "protrusion" or "wire protrusion") 28A, a wire stop 27, and tube depth-control collar 22. In particular, the proximal end of the clearing stem 26 comprises a clearing stem magnet 33 and a Luer clearing stem fitting 32 (FIGS. 3-3A). The control box 1 includes a Luer clearing stem connector 6 (FIGS. 2-2A) along with a motor magnetic coupler 13 which itself includes an internal magnet 12 in the coupler bore. To releasably secure the clearing stem 26 to the control box 1, the clearing stem magnet 33 is passed through the Luer clearing stem connector 6, through a diaphragm 9 and into the motor magnetic coupler 13 where the clearing stem magnet 33 and magnet 12 come into contact to form the magnetic coupling. The Luer clearing stem fitting 32 and Luer clearing stem connector 6 are then engaged to form the Luer lock configuration. Advantages to this magnetic connector include: the omission of threads (which can suffer from stripping), the avoidance of any special tools to facilitate connection, reduced occurrence of bio-contamination, and the avoidance of having to disassemble any portion of the control box 1 in order to switch clearing stems 26. The design of the mechanical components and the strength of the two magnets 33/12 are critical to avoid detaching the clearing stem 26 when the motor 14 is reciprocating. By way of example only, the magnets 12/33 may comprise rare earth magnets (e.g., neodymium) for holding the clearing stem wire 28 to the motor shaft 15. The appropriately-sized magnets may provide from 0.5 to 3.0 lbs of holding force. The sheath is held fast to the control box 1 by the Luer lock connector/receptacle combination. It should be understood that clamping of the sheath 30 needs to have a certain force to secure the sheath 30, but not crush the sheath 30. The stiffness of the sheath 30 must be adequate to preserve the inner diameter cross section during operation. This is necessary to ensure the wire 28 is not pinched by the operator and its motion impeded. The wire 28 must also be flexible enough to navigate a small radius of curvature, such as 2.54 cm radius, while maintaining operation, as can be seen in FIG. 4. In particular, FIG. 4 depicts a clog 40 blocking the tube inner lumen 41 of an artificial tube 39 and wherein the clearing stem 26 navigates a tight radius of curvature, R, and clears the clog 40 which is located past the radius of curvature R. The magnets 33/12 may be cylindrical in shape and the magnet 12 within the motor magnetic coupler 13 is recessed within the motor magnetic coupler 13 that fits over the motor shaft 15. The magnet recess 12A keeps the magnet from sliding along its surface plane and becoming detached while it is reciprocating. A sensor (magnetic or contact, not shown) may also be implemented to illuminate an indicator 75A (e.g., an LED, see FIGS. 2A and 17A) on the control box 1 to confirm that the magnetic connection is securely made. This feature also alerts the user if the connection becomes broken during use.

In an alternate embodiment, the magnet 33 (or 12) may only be located on one of the mating pieces, and a disc or cylinder of magnetic material, be located on the other.

It should be understood that this magnetic Luer lock coupling is by way of example only. It is within the broadest scope of the invention to include other types of releasably securable connector mechanisms, such as, but not limited to, threaded couplings.

Figure 16A:
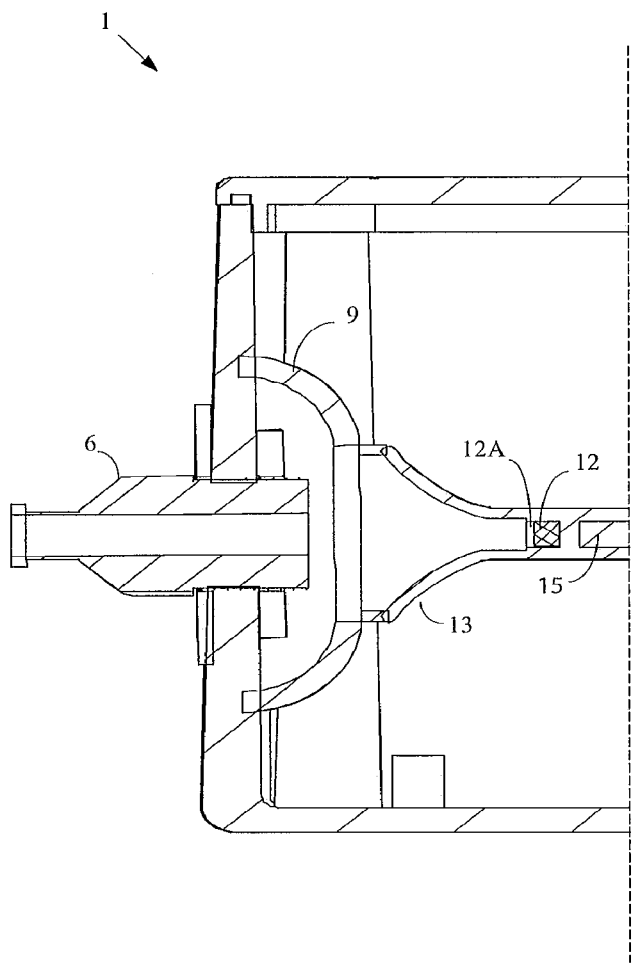
FIG. 16A is a partial end view of the drive side of the control box depicting a sealing diaphragm.

As mentioned previously, the control box 1 includes a diaphragm 9 which seals the control box 1 from contamination from the outside. As can be seen most clearly in FIGS. 2-2A, the diaphragm 9 permits magnetic attachment of the clearing stem 26 so that the magnets 33/12 can make contact while at the same time sealing the box 1 such that no debris, biological or other, enters the control box 1. FIG. 16A is an enlarged partial view showing the sealing diaphragm 9 that does not interfere with motor shaft 15 motion. The diaphragm 9 prevents, among other things, the ingress of liquids into the control box 1. The diaphragm 9 may also be located externally or on the boundary of the control box 1 so that it can be cleaned more easily.

Figure 16B:
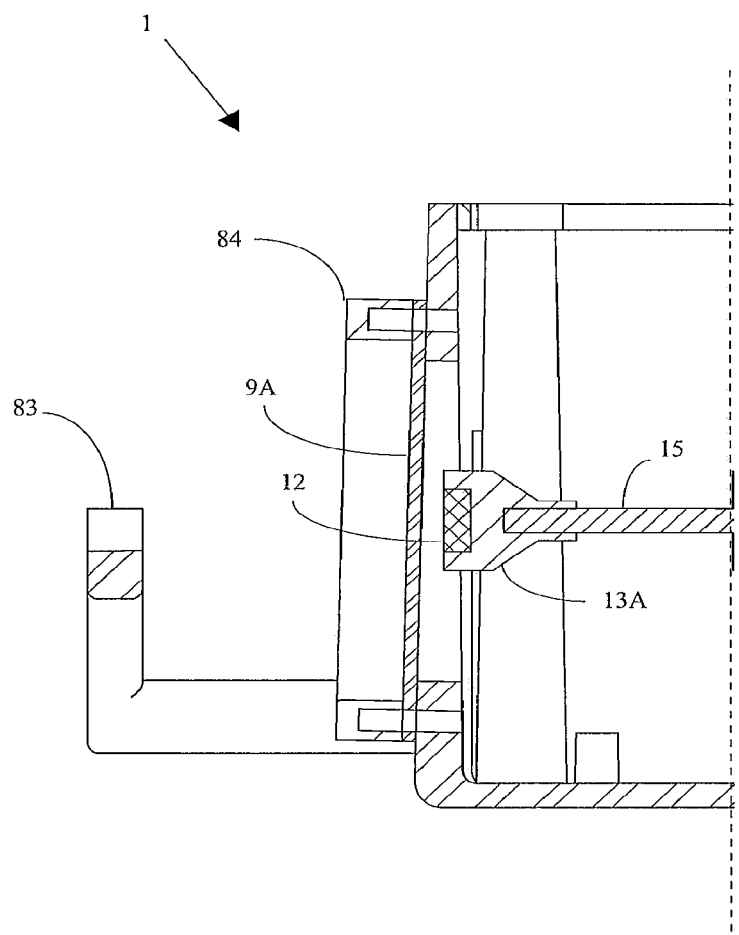
FIG. 16B is a partial end view of the drive side of the control box depicting an alternative clearing stem coupling and sealing diaphragm configuration.
Figure 16C:
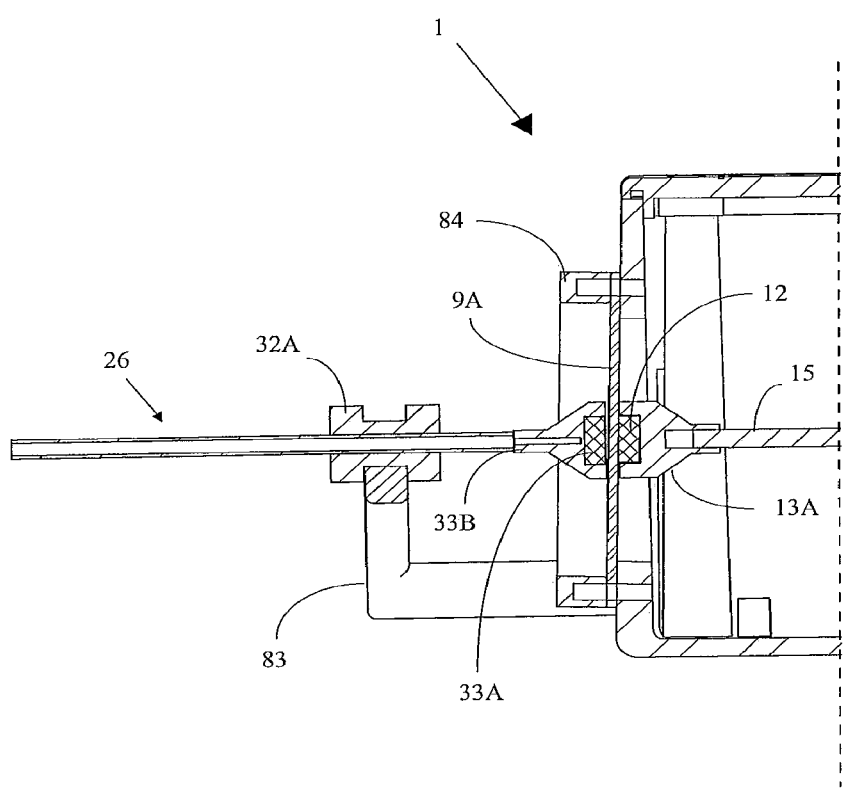
FIG. 16C is a partial end view of the drive side of the control box of FIG. 16 showing the clearing stem being engaged with the control box of FIG. 16B.

As also mentioned previously, the preferred control box 1 is that shown in FIG. 2B wherein a preferred novel clearing stem-control box interface is used. In particular, FIGS. 16B-16C depict the drive side of the control box 1 which includes a sheath attachment bracket 83, an alternate diaphragm 9A, a diaphragm sealing ring 84 (see also FIG. 2B), the motor (e.g., voice coil motor, VCM) shaft 15 along with an alternate motor magnetic coupler 13A (e.g., a magnetic coupler for a VCM). As can be seen from FIG. 16B, the alternate diaphragm 9A contains no holes or apertures through which the clearing stem 26 passes. The diaphragm sealing ring 84 secures the compliant alternate diaphragm 9A in place. To facilitate coupling the clearing stem 26 to this control box, as can be seen most clearly in FIG. 16C, the proximal end of the clearing stem 26 comprises an alternate clearing stem fitting 32A and an alternate clearing stem magnet 33A positioned within an alternate clearing stem magnetic fitting 33B. In order to couple the clearing stem 26 to the control box motor 14, the alternate clearing stem magnet fitting 33B is brought into close proximity with the alternate diaphragm 9A such that the two magnets 12 and 33A are magnetically coupled and abutting through the alternate diaphragm 9A. Thus, there is no breach of the seal of the control box 1 because the alternate diaphragm 9A remains closed. Simultaneously, the alternate clearing stem fitting 32A is secured in the sheath attachment bracket 83. As a result, reciprocation of the motor shaft 15 can occur without passing through any aperture or opening in the alternate diaphragm 9A. FIGS. 1 and IA depict a drive-end view of the clearing stem 26 coupled to the control box 1.

As can be appreciated from FIG. 3A, the wire stop 27 limits the amount of travel of the wire 28 to the right (i.e., towards the motor 14) during operation. In an alternate embodiment, as shown in FIGS. 3C and 3D, the wire stop 27 has been removed and instead an alternate wire stop 27A is used closer to the proximal end of the clearing stem 26. This alternate wire stop 27A comprises a stretchable/pliant (e.g., silicon) tube whose ends are bonded to the alternate clearing stem fitting 32A on one side and to the alternate clearing stem magnet fitting 33B on its other side. This alternate wire stop 27A supports the wire 28 that passes through it. During operation, the alternate wire stop 27A compresses and expands accordingly without interfering with wire 28 oscillation/travel. This alternate wire stop 27A is preferred because it is located externally of the artificial tube 39 and thereby avoids having a stop at the working end of the wire 28 that could interfere with operation. Thus, the alternate wire stop 27A serves to keep the wire 28 from sliding out of the sheath 30.

As shown in FIG. 3A, the wire tip 29 of the wire is rounded to allow the wire 28 to break up a clog 40 (FIG. 4), and to resist penetrating an organ (e.g., stomach or other tissue/organ, etc.) should the wire tip 29 ever make its way close to an organ. The wire protrusion 28A may also be given added flexibility by design compared to that of the rest of the wire 28, to further reduce the risk of the clearing stem wire tip 29 having enough force to penetrate an organ (e.g., the stomach) and/or to increase displacement at the wire tip 29 and facilitate clearing of the clog 40. As mentioned previously, the length of the wire protrusion 28A beyond the end of the sheath 28 and the roundness of the wire tip 29 strongly impact the ease of insertion into an artificial tube. Ideally, the wire tip 29 radius is 0.5 to 2.0 times the overall wire 28 diameter. The stiffness of the sheath 30 comprises a balance between being stiff enough to prevent the operator from clamping down on the wire 28 and stopping wire 28 motion versus being flexible enough to enter an artificial (e.g., feeding) tube 39 and to navigate curves in the tube inner lumen 41 of the artificial tube 39.

Another safety feature of the present invention TCI is that the force generated at the end of the wire tip 29 is less than 5% of the force generated at the motor 14 and therefore, this force reduction provides a safety feature of avoiding puncturing an organ accidentally but yet providing sufficient force to break up the clog 40 and helping to clear the walls of the tube.

As mentioned previously, a stem stiffener 31 (FIGS. 3-3A) is provided at the proximal end of the clearing stem 26 which prevents the operator from over-bending the clearing stem 26 and thereby stopping the reciprocation. The stem stiffener 31 may be constructed of the same material (of a larger diameter than the wire 28 or sheath 30), may be integrated into the sheath 30 via custom extrusion, or may be constructed of a different material, such as any polymer or metal.

To prevent the "over-insertion" of the clearing stem 26, a tube depth-control collar 22 (FIGS. 3-3A and 9A-9C) is provided. The tube depth-control collar 22 comprises a tube depth-control collar body 24 which includes an internal spring 25. A tube depth-control collar push button 23 is provided to lock or unlock the tube depth-control collar 22. In particular, as shown most clearly in FIG. 9A, the depth control collar push button 23 has a central passageway of push button 23A and the tube depth-control collar body 24 has a central passageway of collar body 24A. A spring 25 acts to misalign these two passageways 23A/24A. Thus, to re-position the tube depth-control collar 22 along the length of the sheath 30 (not shown), the depth control collar push button 23 is depressed which momentarily relieves any clamping force on the sheath 30 and the tube depth-control collar 22 can then be moved. When the operator wishes to lock the tube depth-control collar 22 in position, he/she releases the tube depth-control collar push button 23 which results in the sheath 30 being clamped between an upper portion of collar body 24B of the tube depth-control collar body 24 and a lower portion 23B of the tube depth-control collar push button 23. The force applied by the depth-control collar to the sheath 30 needs to be compressive enough to hold the tube depth-control collar body 24 in place against the sheath 30, but not to clamp the sheath 30 onto wire 28. Sheath length markings 30A (FIG. 3B) and integer markings 30B (FIG. 3B) are provided to facilitate positioning the tube depth-control collar 22 along the length of the sheath 30 depending on the length of the artificial tube 39 being cleared. The markings 30A/integers 30B are in ascending or descending order from the distal end 30C of the sheath 30 to the proximal end 30D. Along with the stiffness of the sheath 30, the spring constant of the spring 25 comprises a balance between the force necessary to maintain the tube depth-control collar body 24 in place on the sheath 30 while avoiding the tube depth-control collar body 24 from clamping down on the wire 28 and stopping wire 28 motion.

Figures 9A, 9B, 9C:
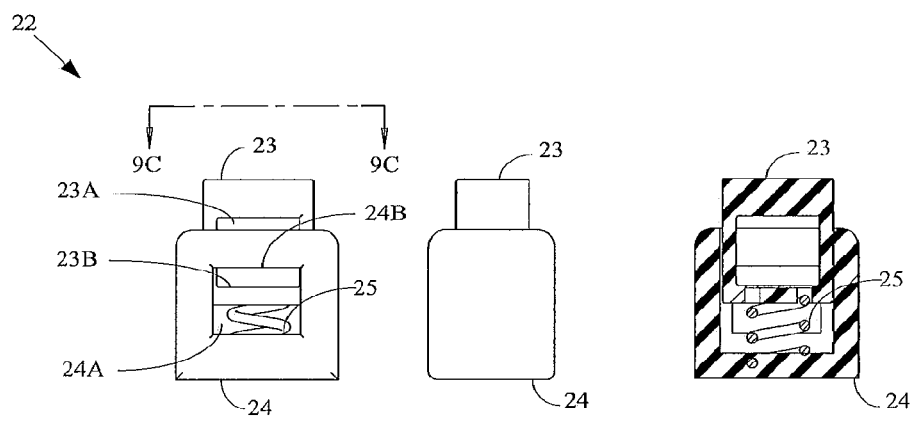
FIG. 9A is a top view of the tube depth-control collar.
FIG. 9B is a side view of the tube depth-control collar.
FIG. 9C is a cross-sectional view of the depth-control collar taken along line 9C-9C of FIG. 9A.
Figure 9D:
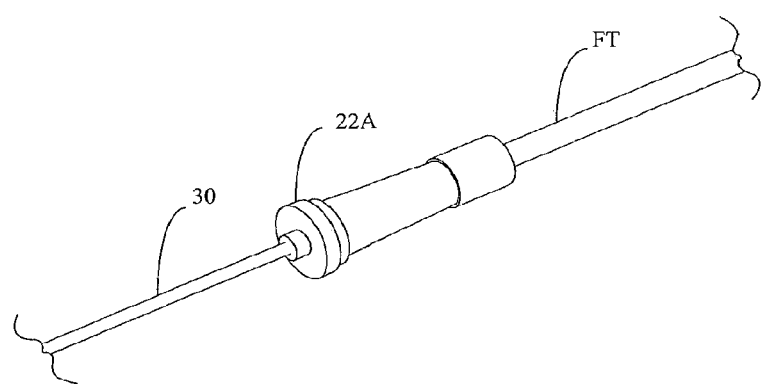
FIG. 9D is a partial isometric view of a fixed tube depth-control collar with the clearing stem inserted into a feeding tube.
Figure 10A:
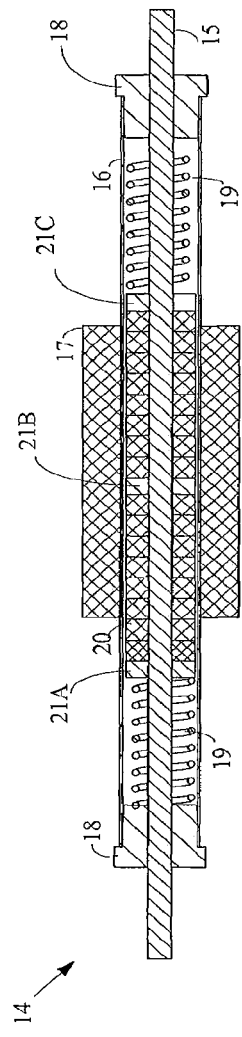
FIG. 10A is a cross-sectional view of the VCM taken along line 10A-10A of FIG. 10.
Figure 10:
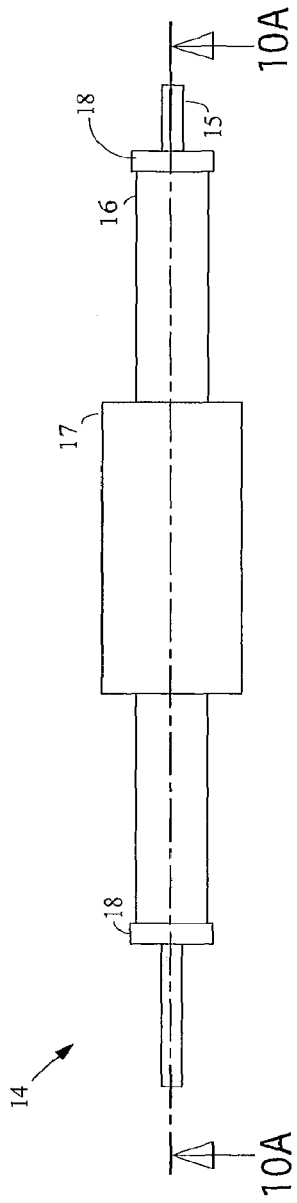
FIG. 10 is a plan view of an exemplary voice coil motor (VCM) for use in the present invention.

It should be understood that it is within the broadest scope of the present invention to include fixed tube depth-control collars 22A, such as that shown in FIGS. 3C, 3D and 9D. In particular, a plurality of clearing stems 26 may be provided, each having a fixed tube depth-control collar 22A fixed at a predetermined length (e.g., 35 inches, 44 inches, etc.) along the sheath 30. FIG. 9D shows the fixed tube depth-control collar 22A abutting the proximal end of the feeding tube FT thereby preventing the sheath 30 from entering any further within the feeding tube FT. Using this embodiment, the operator selects one clearing stem 26, from a plurality of clearing stems 26, having a particular fixed tube depth-control collar 22A and clearing stem 26 length that is appropriate for the particular feeding tube FT that contains a clog that is to be cleared.

Figures 6, 7, 8:
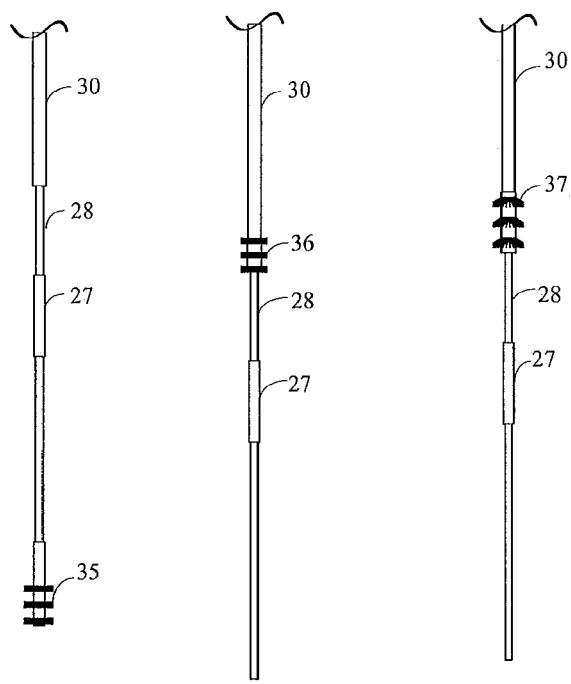
FIG. 6 is a partial view of the clearing stem whose distal end includes a brush mounted on the wire tip.
FIG. 7 is a partial view of the clearing stem whose distal end includes a brush mounted on the distal end of the sheath.
FIG. 8 is a partial view of the clearing stem whose distal end includes a brush mounted on the distal end of the sheath with bristles swept toward the extreme distal end of the stem.

To facilitate clearing, a brush may be included on the wire tip 29 or on the distal end of the sheath 30. For example, FIG. 6 depicts a wire tip brush 35 on the end of the wire 28 whereas FIGS. 7 and 8 depict respective brushes with sheath tip brush 36 and forward swept sheath tip brush 37 on the end of the sheath 30. Therefore, as the wire protrusion 28A reciprocates, the wire tip brush 35 cleans the tube walls or when the sheath 30 is inserted into the artificial tube 39, the insertion motion causes the brush 36 or 37 to clean the tube walls, as well as facilitate the movement of the dislodged blockage and/or its pieces. In particular, the small brush (e.g., polyester, foam, or twisted in wire) on the distal end of sheath (36 or 37) or wire (35) provides more thorough clearing of tube walls. With particular regard to brush 36 or 37, mounted on the distal end of the sheath 30, the brush 36 or 37 is non-moving in this embodiment, which helps to clear excess particles from tube walls after the wire protrusion 28A has cleared the clog 40 and as the sheath 30 is retracted and moved out of the artificial tube 39. The advantage of the brush 36 or 37 on the sheath 30 is that the brush 36 or 37 does not impede the wire 28 motion at all. It should be noted that the forward swept sheath tip brush 37 on the distal end of the sheath 30 shown in FIG. 8 includes bristles that are swept in the distal direction. This makes clearing effective as the forward swept sheath tip brush 37 is inserted into the tube, but also allows for a smoother retraction because the sweep-direction of the bristles reduces the resistance of the forward swept sheath tip brush 37 when the operator is removing the clearing stem 26 from the artificial tube 39. This reduced resistance minimizes the chance of dislodging the artificial tube 39 from the patient when the clearing stem 26 is removed.

Figures 5A, 5B, 5C, 5D:
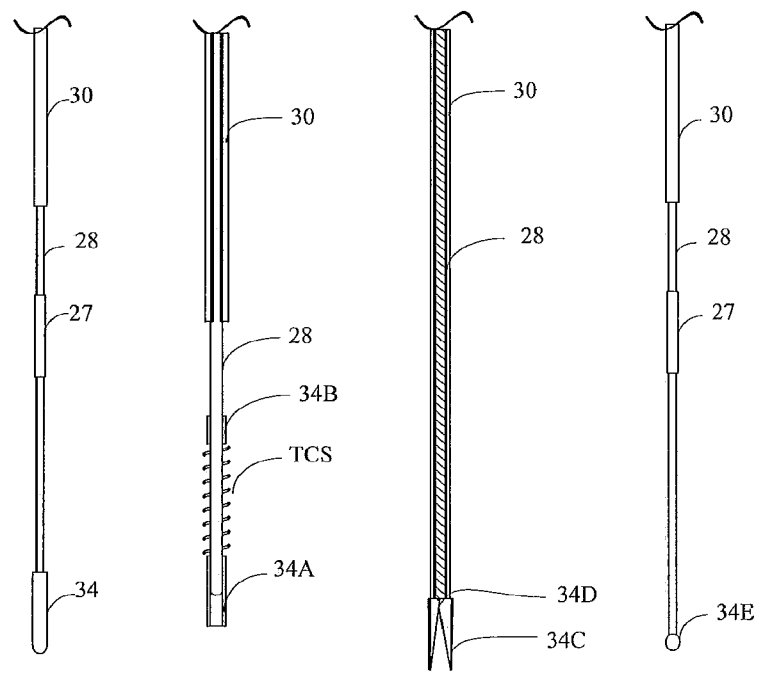
FIG. 5A is a partial view of the clearing stem whose distal end includes a plastic clearing tip on the distal end of the wire.
FIG. 5B is a partial cross-sectional view of the clearing stem whose distal end includes an alternative hollow cylindrical clearing tip on the distal end of the wire including a tip compression spring (TCS)
FIG. 5C is a partial cross-sectional view of the clearing stem whose distal end includes an alternative clearing tip on the distal end of the wire including a gripping or chopping mechanism.
FIG. 5D is a partial view of the clearing stem whose distal end includes an alternative clearing tip on the distal end of the wire includes a welded ball.

Other configurations of the clearing stem 26 include a range of wire tip 29 designs. For example, a sphere (e.g., metal or plastic) anywhere along the length of the wire protrusion 28A may be included, such as the ball tip 34E in FIG. 5D. If the sphere is included at the wire tip 29, this helps prevent the inadvertent insertion into an organ (e.g., stomach) wall, and also prevents the inadvertent retraction of the wire protrusion 28A into the sheath 30 during use, setup or clearing illustrated in FIG. 5D. Another alternative end may comprise a plastic end wherein a plastic tip is fused or ultrasonically welded to the wire tip 29 and which may comprise the shape of a point, helix, or radius, etc., illustrated in FIG. 5a. In addition, these alternative tips may further comprise ridges or a pattern designed to sweep broken debris away from the clog 40 site. FIG. 5A depicts the distal end of the wire 28 with a plastic wire tip 34. An alternative tip design may include a spring guide wire design possibly exemplified by Lake Region Medical Paragon Pre-coat guide wires. Another alternative tip could be flexible such as a Tecoflex® tip which causes the tip to slide across contacted tissue rather than puncturing tissue, thus providing an additional safety feature.

FIG. 5B depicts another alternative end which may comprise a small spring mechanism which provides increased displacement and protection against an over-insertion puncture. In particular, a plastic or metal alternate tubing tip 34A is positioned over the distal end of the wire 28. The rear end of the alternate tubing tip 34A is secured to one end of a tip compression spring TCS that is slid onto the wire 28. A fixed member 34B is secured to the wire 28 and to the other end of the tip compression spring TCS. Thus, the alternate tubing tip 34A acts as a further protection against accidental contact with soft tissue, since the alternate tubing tip 34A can only be retracted when it encounters a solid object, e.g., a clog, and whereby the wire tip 29 is then exposed to the solid object. Once the clog is cleared, the alternate tubing tip 34A springs back in position ahead of the wire tip 29 to shield it from contact with bodily tissue or organs. Moreover, the wire tip 29 may also comprise a small gripping mechanism wherein the wire tip 29 contains a small cable-actuated gripping mechanism to dislodge clogs 40 or retrieve samples of clog material. In particular, FIG. 5C depicts gripping/chopping mechanism 34C that are hinged or pivoted at pivot point 34D. By actuating a control member (not shown, e.g., a cable, rod, electromechanical motor, piezoelectric motor etc.), the gripping/chopping mechanism 34C can be closed around a clog specimen or used to tear away the clog material to dislodge clogs or retrieve a sample of the clog material.

An alternative design to the wire 28 is the provision of a flexible portion of wire 28 located between the end of the sheath 30 and the wire tip 29. Thus, the wire protrusion 28A may comprise a material that is more flexible than the remaining part of the wire 28 that couples to the motor shaft 15.

Control Box Motor for TCI

As mentioned previously, the motor 14 drives the wire 28, creating linear displacement. The back and forth displacement of the wire 28 allows it to break up and clear clogs 40 in artificial tubes (e.g., enteral feeding tubes and especially NG feeding tubes), while simultaneously cleaning debris from the tube walls. The wire tip 29 of the wire 28 has a linear displacement, preferably, in the range of 0.25 to 25 mm, more preferably 2-10 mm from the distal end of the sheath 30. The frequency of operation of the motor shaft 15 preferably varies from 10 to 100 Hz but more preferably in the 15-40 Hz range. The motor 14 has a range of displacement preferably from 1-40 mm and more preferably in the range of 10-30 mm. The motor blocking force (i.e., the maximum force output) has a preferable range of 2-25N and more preferably 6-14N.

The reciprocating motion of the clearing stem 26 of the present invention TCI can be achieved using a variety of motor technologies, such as, but not limited to, voice coil motors (VCMs) as illustrated for the motor 14 (FIGS. 2-2B, 10-10A and 15), DC motors 49 (FIG. 11, 11A-11C), piezoelectric transducers, including amplified piezoelectric actuator motors 59 (APA, such as those disclosed in U.S. Pat. No. 6,465,936 (Knowles, et. al), whose entire disclosure is incorporated by reference herein) (FIGS. 12-12A), piezoelectric actuators, active polymer compound actuators, solenoid motors 55 (FIGS. 13-13A), pneumatic motors 42 (FIGS. 14-14A), magnetorestrictive transducers, electrorestrictive transducers, etc.

As shown in FIGS. 2-2A, 10-10A, and 15 the motor 14 may comprise a voice coil motor (VCM) having a VCM body 16 mounted within end bearings 18, a displaceable motor shaft 15, dampers or spring 19, and magnets 20 mounted to the motor shaft 15, with pole pieces 21A, 21B and 21C (FIGS. 2A, 10A and 15) located at the ends and within the center of the magnets 20. Coil windings 17 are wound around the VCM body 16 and thus do not interfere with VCM motor shaft 15 displacement. Motor mounts 7 and motor mount dampers 8 secure the motor 14 within the control box 1 while avoiding direct coupling against the bottom surface of the control box 1. A motor printed circuit board (PCB) 11 distributes the current commands from the electronics 10 to the coil windings 17 through wires 53. When an electric current is applied through the coil windings 17, a magnetic field, due to Ampere's Law, is produced inside the coil windings. The non-uniform magnetic field at the ends exerts a force on the permanent magnets 20. Alternating the current alternates the direction of the magnetic field gradients and results in a reciprocating motion of the motor shaft 15 with respect to the VCM body 16. The magnitude of the force is determined by the magnetic flux density, which is proportional to the number of turns per length of the coil, current magnitude, cross-sectional area of the coil, as well as the strength of the permanent magnets 20. The springs 19 absorb the energy associated with abrupt changes in the direction of the inertial force of the magnets 20 and VCM body 16 when actuated, resulting in a lowering of vibration and increasing the tube clearer TCI usability and efficiency.

By way of example only, the spring constant of the springs 19 can range from 0.5-5 lb/in, and more preferably 1.5-2.5 lb/in.

A soft stop SS may be installed at the free end of the VCM motor shaft 15 because the shaft tends to drift off center during use.

Figure 15:
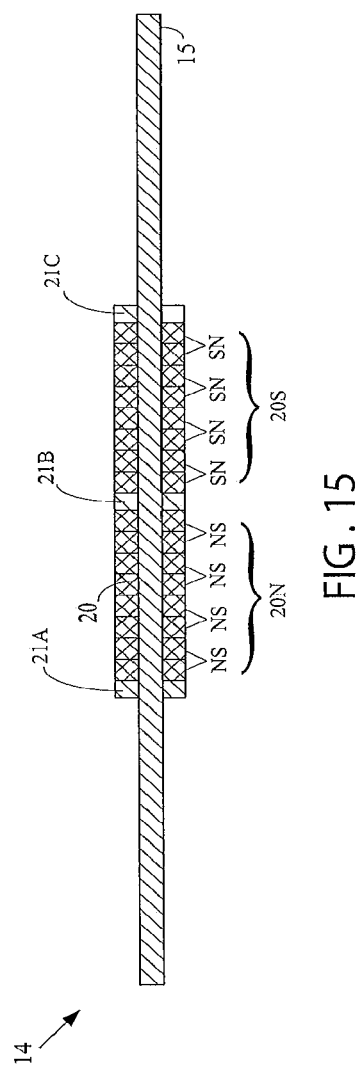
FIG. 15 is a cross-sectional view of the magnetic pattern used in the VCM showing driving members having opposite pole directions.

A further variation of the use of a plurality of magnets is to arrange the plurality of magnets into two "driving members" disposed between the pole pieces 21A-21C, mentioned previously. Pole pieces 21A-21C are typically ferromagnetic and are preferably stainless steel. As shown most clearly in FIG. 15, the south poles of the first magnetic driving member 20N and the south poles of the second magnetic driving member 20S are fixedly secured to the opposing faces of the pole piece 2 IB in order to provide a zone of maximum magnetic flux density which extends radially outwardly from the central portion of the pole piece 21B, similar to the configuration disclosed in U.S. Pat. No. 4,363,980 (Peterson) whose entire disclosure is incorporated by reference herein. Alternatively, each magnetic driving member 20N and 20S may be replaced with a single elongated permanent magnet, rather than using a plurality of magnet elements as shown in FIG. 15. In either case, the driving members 20N and 20S have opposite pole directions.

It is within the broadest scope of the present invention that the relative positions of the coil windings 17 and the magnets 20 are reversed (not shown), i.e., the coil windings 17 are wound directly around the motor shaft 15 and the magnets 20 are positioned around the VCM body 16 and thus do not interfere with the motor shaft's 15 reciprocation.

Alternatively, a dual coil motor or actuator (also not shown) is also within the broadest scope of the present invention. In particular, instead of using magnets 20, two coil windings are used wherein one coil is wound directly around the motor shaft 15 and a second or outer coil is wound around the first or inner coil but without interfering with shaft displacement. Each coil is supplied with respective alternating current sources which generate respective electromagnetic fields that also generate a reciprocating motion of the motor shaft 15. The inner coil may conduct direct current DC while the outer coil conducts alternating current AC. Alternatively, the inner coil may conduct alternating current AC while the outer coil conducts direct current DC, or both the inner coil and the outer coil may conduct alternating current AC.

Moreover, to reduce vibration caused by the oscillating motion of the motor shaft 15, a secondary VCM or counter balance mechanism 14A of similar size (also referred to as a "countermass" or "counterbalance") may be included and driven at an opposite phase (e.g., 180° phase lag) for cancelling vibration caused by the motor 14. See FIG. 2B. Thus, when the tube clearer TCI is operated such that the first VCM is activated to cause the motor shaft 15 to move, a first momentum vector is produced. The second VCM is operated such that it creates a second momentum vector equal in magnitude but opposite in direction to the first momentum vector, such that the net sum of the first and second momentum vectors is minimized and preferably equal to zero. In particular, to maximize vibration reduction, the moving parts (shaft, magnets, pole pieces, attachments, etc.) of the counter balance mechanism 14A should have a moving mass and velocity (frequency and displacement) equal to that of the moving parts of the actuating motor 14. This is based on the principle of Conservation of Momentum. The sine waves that actuate both VCMs must have a 180 degree phase lag between them. This causes their forces to be opposite and (ideally) equal, cancelling each other out. As such, operation of the tube clearer TCI does not cause "chatter" and therefore there is no irritation to the operator or patient.

DC Motor 49

Figure 11:
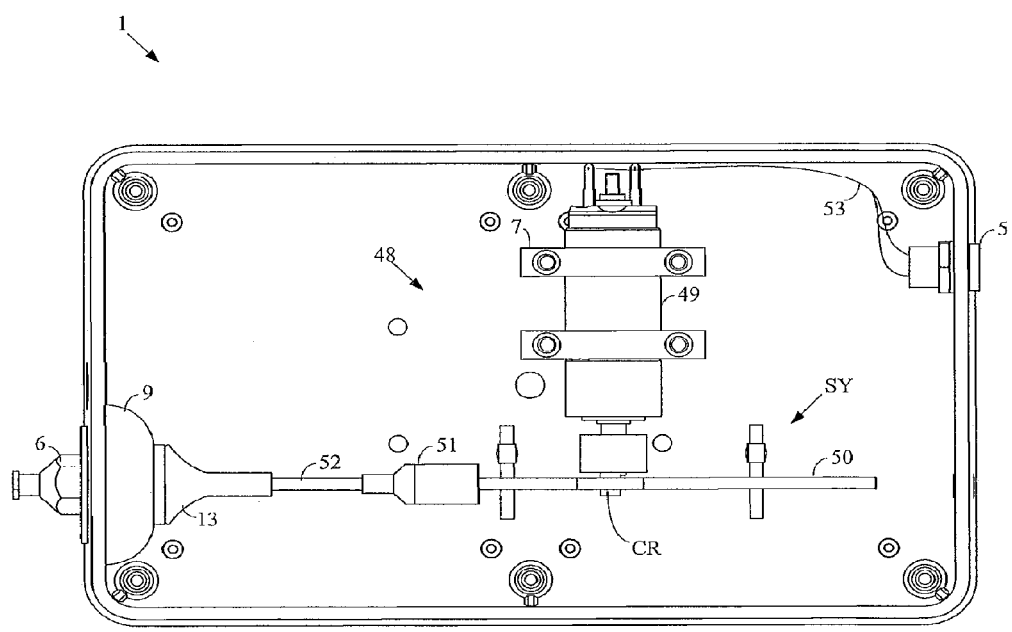
FIG. 11 is a top plan view of another exemplary motor of the present invention with the lid removed and depicting a DC motor that drives a scotch yoke.
Figure 11A:
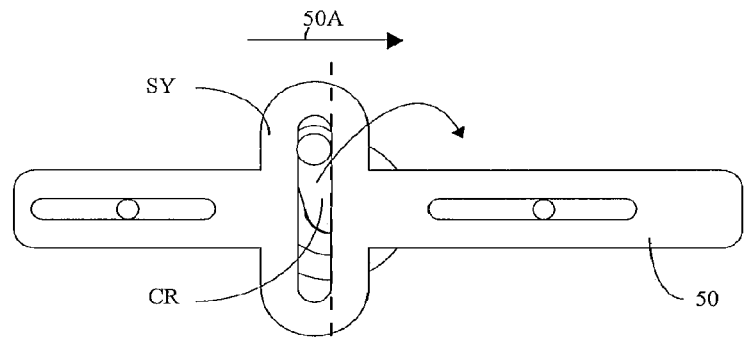
FIGS. 11A-11C depict a sequence of the scotch yoke operation of FIG. 11.
Figure 11B:
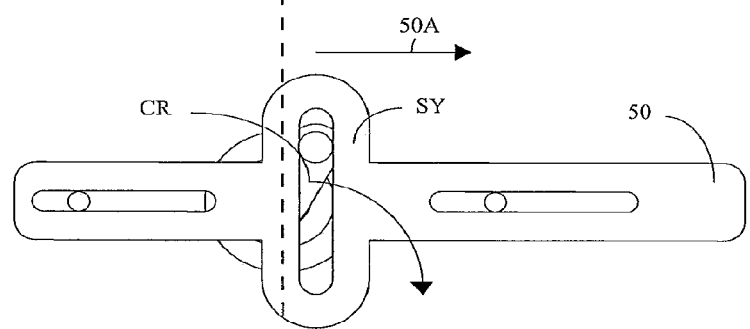
Figure 11C:
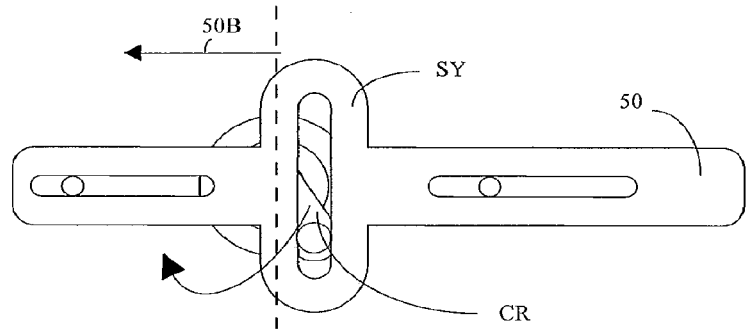

The motor may also comprise DC or DC brushless motor 49 for creating reciprocating displacement via a scotch yoke SY or similar mechanism. FIG. 11 depicts the control box 1 using a DC motor 49 and scotch yoke SY as the actuating mechanism. No signal generating electronics are needed for this application since the DC motor 49 is simply turned on to cause a rotating crank CR to drive the scotch yoke slider 50 and the scotch yoke shaft 52 in reciprocating motion. The adapter 51 transmits the scotch yoke SY motion to the scotch yoke shaft 52. FIGS. 11A-11C show three still frames as an example of scotch yoke SY motion. FIG. 11A and FIG. 11B show Scotch yoke forward displacement direction 50A and FIG. 11C shows Scotch yoke rearward displacement direction 50B are moving in a reciprocating motion.

APA Motor 59

Figure 12A:
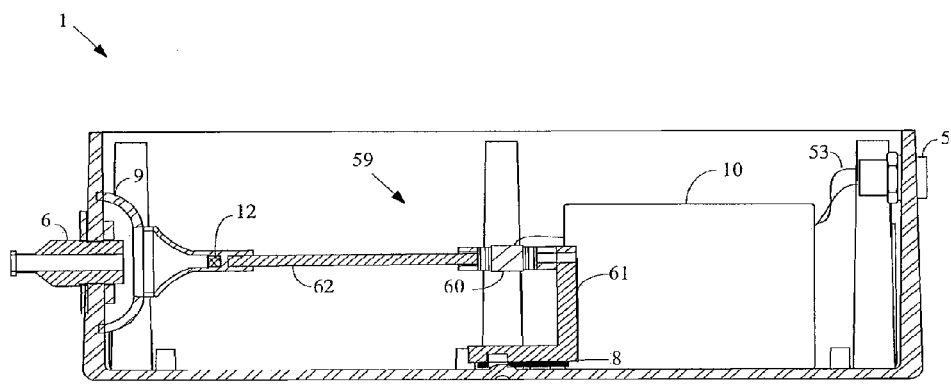
FIG. 12A is a cross-sectional view of the APA control motor taken along line 12A-12A of FIG. 12.
Figure 12:
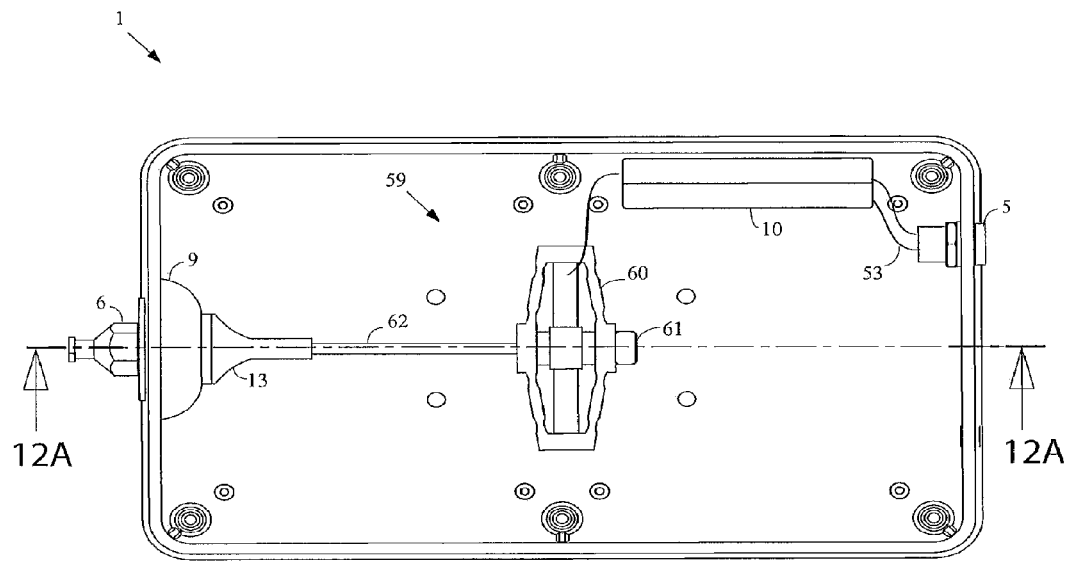
FIG. 12 is a top plan view of another exemplary motor of the present invention with the lid removed and depicting an amplified piezoelectric actuator (APA)

An amplified piezoelectric actuator (APA) 60 creates reciprocating displacement in the lower range, preferably (0.1 to 2.0 mm), anchored to the control box 1. One or more APA motors 59 can be used in series, as this increases displacement. FIGS. 12-12A depict the control box 1 with an APA as the actuating mechanism. In particular, the APA actuator 60 is mounted to the control box via an actuator mount 61 which is indirectly coupled to the control box 1 bottom via motor mount damper 8. An actuator shaft 62 conveys the reciprocating motion, from APA actuator 60 expansion and contraction, to the clearing stem (not shown) via the magnetic coupling discussed earlier for the other embodiments.

Langevin Transducer 77

Figure 12B:
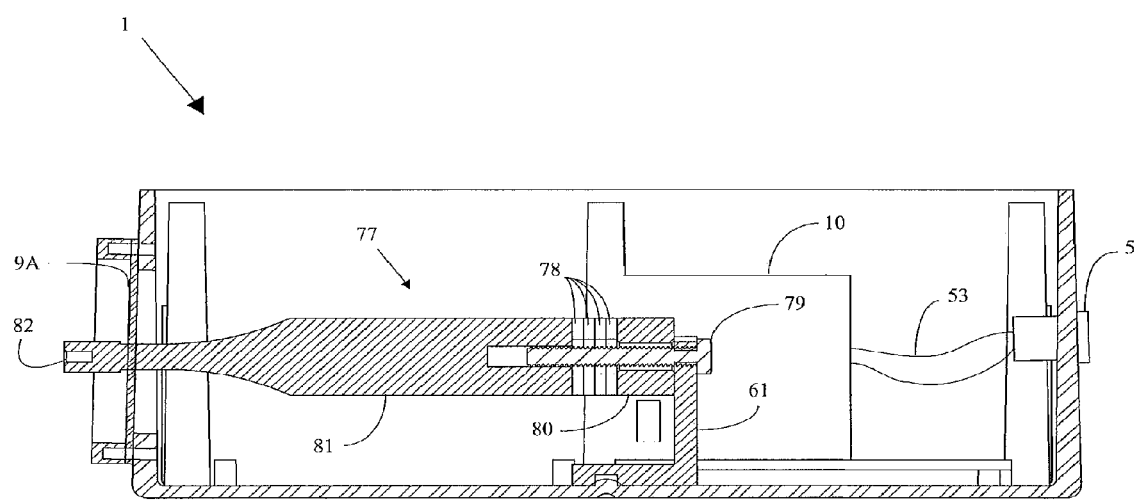
FIG. 12B is a cross-sectional view of Langevin transducer control motor.

A Langevin transducer 77 can be used for the motor 14. As shown in FIG. 12B, the Langevin transducer comprises a plurality of piezoelectric elements 78 are arranged to cause a horn 81 to vibrate to form the reciprocating motion. The horn 81 is secured to an actuator mount 61 using a pre-stress bolt 79. The Langevin transducer 77 includes a tail mass 80 for bolt-clamping the Langevin transducer 77 to the actuator mount 61. The forward end of the horn 81 is tapered such that a distal end of the horn passes through the control box alternate diaphragm 9A. A clearing stem attachment 82 is provided to receive/mate with the clearing stem 26 as discussed previously. A power source (not shown) that provides the proper activation energy is coupled through the power plug 5 and via electronic control wires 53.

Figure 12C:
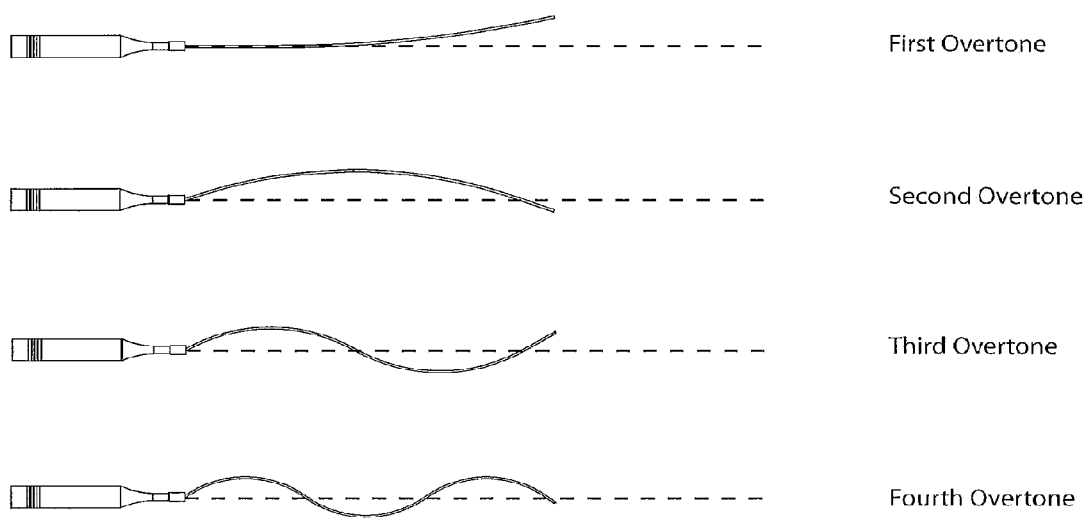
FIG. 12C is a functional diagram depicting the first four overtones of clearing stem motion introduced by the Langevin transducer.

It should be noted that activation of the Langevin transducer 77 creates reciprocating motion with the introduction of several overtones (viz., first-fourth overtones), shown in FIG. 12C. As part of the design of the present invention, the lateral displacement caused by these overtones is kept to a minimum. In particular, the piezoelectric elements 78 (e.g., a plurality of piezoelectric ceramic discs) are held in compression between the tail mass 80 and horn 81; and the pre-stress bolt 79 passing from a proximal end of the tail mass 80 and threading into the horn 81. Vibratory motion is caused by the activation of the piezoelectric elements 78 upon being exposed to an alternating electric field such as from an AC electrical current applied to electrical contacts (not shown) formed on opposing sides of each of the piezoelectric elements 78. The vibratory motion is translated as a standing harmonic wave spanning longitudinally across the horn 81 and to the clearing stem (not shown). Therefore, when operated at ultrasonic frequencies, the Langevin transducer 77 translates the ultrasonic energy as a reciprocating vibration to the clearing stem 26, and produces a standing wave within the flexible member. The horn 81 and tail mass 80 are made of a metal such as titanium, stainless steel or, preferably, aluminum. The pre-stress bolt 79 is generally of stainless steel, but not limited thereto.

Solenoid Motor 55

Figure 13A:
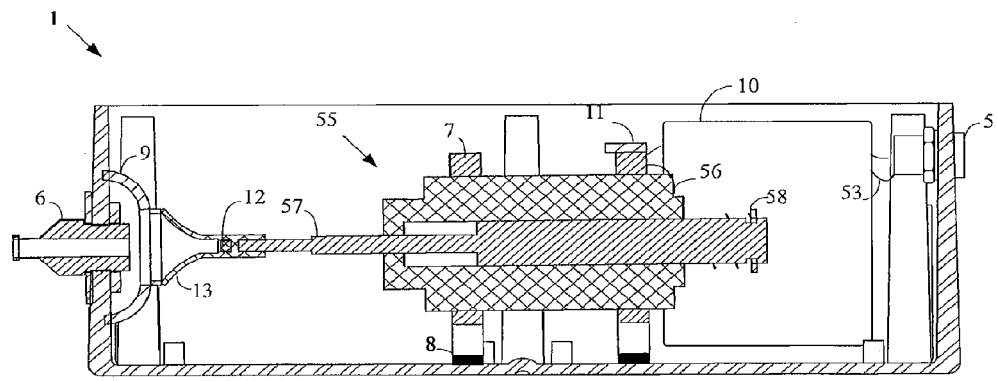
FIG. 13A is a cross-sectional view of the solenoid motor taken along line 13A-13A of FIG. 13.
Figure 13:
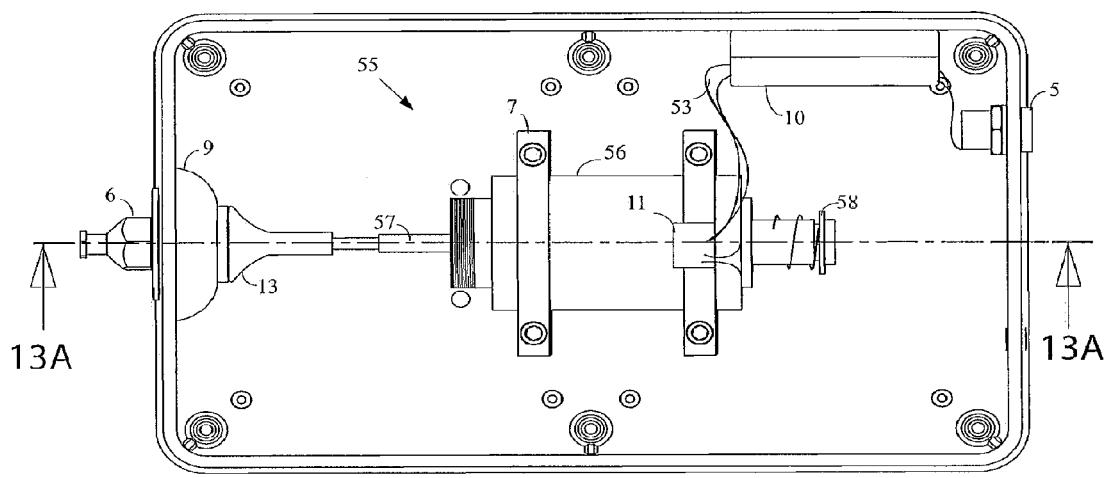
FIG. 13 is a top plan view of another exemplary motor of the present invention with the lid removed and depicting a solenoid.

The solenoid motor 55 shown in FIGS. 13-13A mounted in the control box 1 operates in a very similar manner as does the motor 14, discussed previously. A return spring 58 is required with the solenoid 56 since it has one-way actuation. In particular, the electronics 10 are configured to pulse the solenoid 56 such that during the pulse, the solenoid shaft 57 is driven to the left in FIGS. 13-13A and when the pulse is terminated, the return spring 58 restores the solenoid shaft 57 to the right. This action is repeated at the frequencies discussed previously.

Pneumatic Motor 42

Figure 14A:
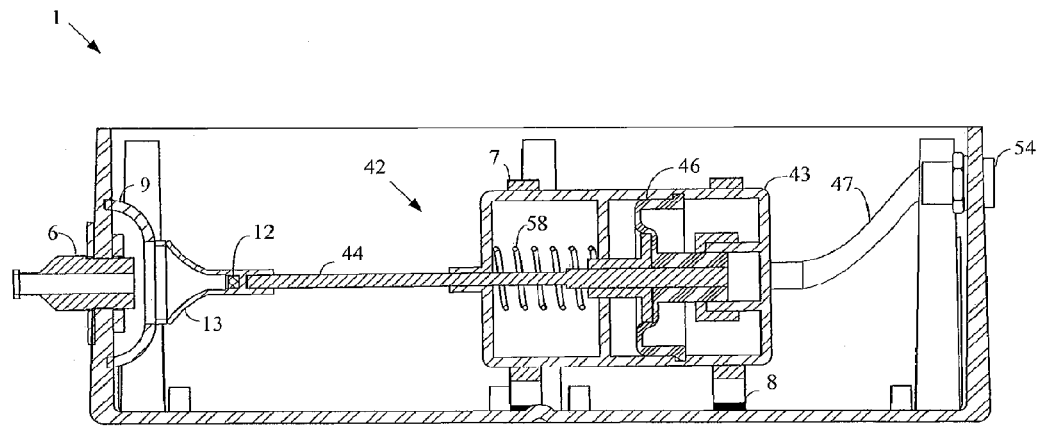
FIG. 14A is a cross-sectional view of the control motor taken along line 14A-14A of FIG. 14.
Figure 14:
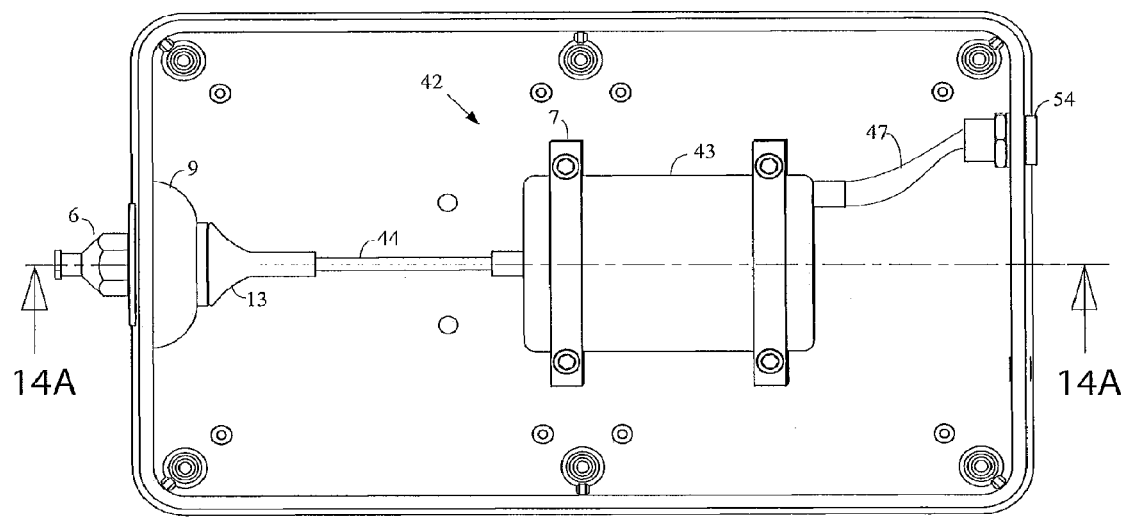
FIG. 14 is a top plan view of another exemplary motor of the present invention with the lid removed and depicting a pneumatic actuator.

FIGS. 14-14A depict a pneumatic motor 42 for creating the reciprocating motion. In particular, the pneumatic motor shaft 44 is driven by the pneumatic motor 42 which receives pneumatic pulses from a pneumatic pulse generator (not shown) via an air supply inlet 54 on the control box 1 and through internal tubing 47. The pneumatic motor 42 is positioned within a pneumatic motor housing 43 which includes a pneumatic motor diaphragm 46 for distributing the pneumatic pulse evenly to the pneumatic motor shaft 44, thereby maintaining its alignment, while at the same time providing a tightly-sealed motor configuration. The pneumatic pulse causes the pneumatic motor shaft 44 to be driven to the left while compressing a return spring 58. Once the pneumatic pulse is terminated, the return spring 58 restores the pneumatic motor shaft 44 to the right. This action is repeated at the frequencies discussed previously.

Electronics

Figure 17A:
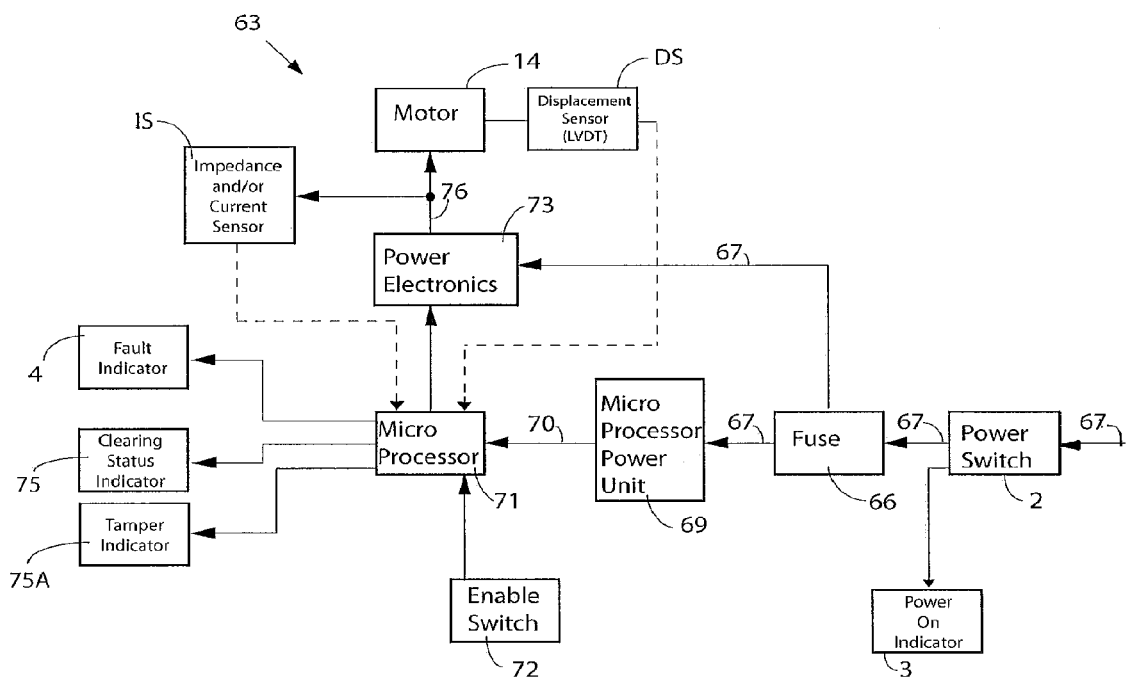
FIG. 17A is a block diagram of the control box electronics for the reciprocating tube clearer (TCI) configuration.

FIG. 17A provides a block diagram of the electronic system 63 contained within the electronics 10. A microprocessor (e.g., MSP430F2618TPMR) controls the power electronics 73 to the motor 14. Although not shown, a power supply (e.g., an Autodyne UL medically-approved power supply AMP6301-08) converts the 120 VAC from the wall outlet to 24 VDC. A microprocessor power unit MPU 69 (e.g., a voltage regulator circuit, such as the LM317/LM337) reduces the incoming (e.g., +24 VDC) power 67 to a lower power (e.g., +3.3 VDC indicated by 70) for use by the microprocessor 71. The microprocessor 71 controls the motor 14 via power electronics 73, as well as all of the associated indicators, such as LED indicators 3, 4, 75 and 75A. The power electronics 73 convert the microprocessor 71 commands into a power signal to motor 76 (24 Vp-p AC) using internal inverters to activate the motor 14. An enable switch 72 is provided to permit the clearing stem to be continuously reciprocated for a predetermined period of time (e.g., 4-20 minutes), which avoids running the device TCI for too long but provides sufficient time to effect clearing the clog. A control box power switch 2 is coupled to the microprocessor power unit (MPU) 69 via a fuse 66. A power indicator (e.g., LED) 3 is provided on the control box 1. When the control box 1 is externally powered, e.g., from 120 VDC, 60 Hz wall power, a power-cord (not shown) is supplied with the control box 1, and which includes an AC/DC converter. It should be understood that this does not limit the operation of the present invention to wall power in any manner and that the control box 1 can be operated off any type of power source, including battery power.

The electronic system 63 may also include a displacement sensor DS (e.g., an LVDT (e.g., Macro Sensors CD 375-500) or force sensor/load cell (e.g., Futek LPM 200); or eddy current sensor (e.g., Micro-Epsilon eddy NCDT 3010), etc.) for accomplishing closed loop motor control as well as detecting changes in the clearing process. For example, the sensor DS forms a closed loop with microprocessor 71 for maintaining the motor shaft 15 in a centered position, which maintains the motor 14 where the force is the greatest and provides optimum control. Alternatively, the sensor DS may comprise a displacement/force feedback sensor or even an optical displacement sensor (e.g., Variohm Eurosensor). The DS sensor output may also be used for self-centering of the wire 28 during operation. As part of the closed loop control, it may be advantageous to also change any DC offset to alter the force profile at the wire tip 29 and to provide more power to one side.

In addition, an impedance sensor/current sensor IS may be included for detecting the change in voltage/current of the motor 14 and communicating with the microprocessor 71 for determining the status of the clearing process, such as initial contact with blockage, passage therethrough, etc. This status can be conveyed through a display or clearing status indicator 75 (e.g., LEDs, 7-segment displays, audible indicators, etc.) or a series of differently-colored LEDs 75 (e.g., from green to yellow to red). Alternatively, where the displacement sensor DS comprises a displacement/force feedback sensor, this sensor's output can be used to detect when the clog 40 is contacted and when it is penetrated.

As mentioned earlier, in order to indicate that the clearing stem magnet 33 and the control box magnet 12 are coupled properly, a magnetic/conductive sensor to determine if a solid clearing stem connection has been made which can then be provided to an indicator 75A. By way of example only, a magnetic sensor could be implemented to determine safe connectivity between magnets in operation, such as a Honeywell Magnetometer, HMR2300. These magnetometers measure both magnetic field intensity and direction using their Anisotropic Magneto-Resistive sensors. The ability to acquire this information can be utilized by the microprocessor 71 to ensure the magnet polarities are correct, and that the magnets field intensity is at a safe level (e.g., they have not been de-magnetized). Similarly, an anti-tamper circuit may also be included in the electronic system 63 which interrupts operation if the control box 1 is attempted to be opened. A corresponding tamper sensor may also be provided that causes the indicator 75A on the control box 1 to indicate if someone has opened, or attempted opening the lid of the control box 1. Furthermore, control box screws can be configured to disable operation of the control box 1, if they are attempted to be removed during activation.

The microprocessor 71 can be programmed to drive the electronic system 63 at the needed voltage and frequency, converting 120V 60 Hz wall power to needed parameters to drive the motor 14 at, for example 15-40 Hz (e.g., 25 Hz). In particular, several fault conditions are programmed into the microprocessor 71 for which it interrupts device TCI operation:

$V_{input}$<20 VDC;
$V_{input}$>25 VDC;
Overtemperature condition pertaining to the amplifier IC;
Short circuit condition pertaining to the amplifier IC;
Should any of these fault conditions occur, the microprocessor 71 activates a fault indicator 4. Also, as discussed earlier, the enable switch 72 permits the operator to initiate the reciprocating motion without the need to hold any trigger. The enable switch 72 permits the control box 1 to maintain the reciprocating motion for a predetermined period of time (e.g., 4-20 minutes) before the reciprocating motion is terminated.

Figure 17B:
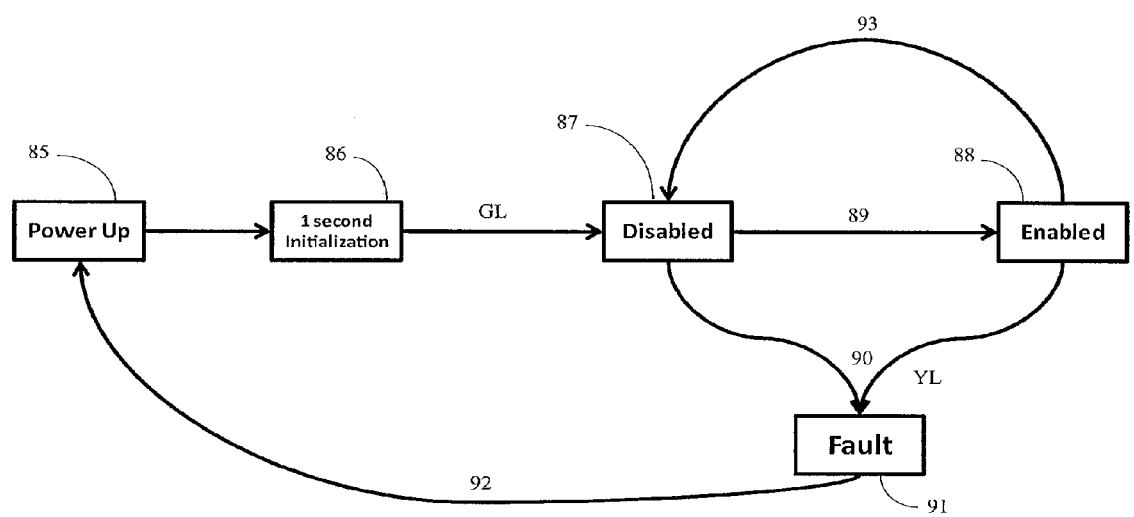
FIG. 17B is an operational flow diagram of the microprocessor of the control box electronics of FIG. 17A.

FIG. 17B provides a flow diagram of the microprocessor 71 operation: at step power up 85, the microprocessor 71 is powered up following activation of the power switch 2 by the operator. The microprocessor 71 then conducts a one second step initialization 86. Once the initialization 86 is completed the microprocessor 71 activates the power indicator 3 (e.g., typically a green light (GL) or indication). At this point, device TCI remains in a disabled state until the enable switch 72 is activated by the operator; "enable button pressed" step 89 of the flow diagram represents activation of the enable switch 72 resulting in the enabled state 88 of the device where the clearing stem 26 is being reciprocated as described previously. The microprocessor 71 then maintains operation of this reciprocation for the predetermined period (e.g., 4-20 minutes) shown as time interval 93 in the flow diagram. At the end of the predetermined period, the microprocessor 71 terminates the reciprocating movement of the clearing stem 26 and returns to step disabled 87. In addition, upon activation of the enable switch 72 by the operator, the microprocessor 71 monitors the device TCI for the faults described above, indicated by the paths-fault detected 90 of the flow diagram. If a fault 91 is detected by the microprocessor 71, the microprocessor 71 terminates clearing stem reciprocation and activates the fault indicator 4 (e.g., typically a yellow light (YL) or indication). The microprocessor 71 then shuts down (step power cycle 92) the device TCI.

Operation of the present invention tube clearer TCI is as follows: if wall power is being used, the connector end of the power cord (not shown) is inserted into power plug 5 (FIGS. 2-2A) on the control box 1 and the other end of the power cord is coupled to a power supply which is coupled to a standard 120V RMS/60 Hz three-prong outlet. The control box 1 is turned on using the power switch 2 which turns on the power indicator 3 which verifies that the control box 1 is operating properly.

A new clearing stem 26 is removed from its packaging (but not discarded since the contaminated clearing stem 26 will be placed in the packaging and then discarded). If a plurality of clearing stems 26 are provided with tube depth-control collars fixed at different positions, the operator needs to select the clearing stem which has the appropriate fixed collar position; if, the tube depth-control collar is adjustable, the operator needs to position the collar appropriately along the clearing stem.

The following discussion of the operation is based upon the control box shown in FIGS. 2-2A, it being understood that this is by way of example only. The wire end of the wire 28 comprising the clearing stem magnet 33 is gently pulled out from within the sheath 30 and then the clearing stem magnet 33 is inserted into the bore of the Luer clearing stem connector 6 until the operator feels the pull of the clearing stem magnet 33 to the other magnet 12 and/or hears the magnets connect. The sheath 30 is then pushed until the Luer clearing stem fitting 32 is flush with the Luer clearing stem connector 6 on the control box 1. The Luer clearing stem fitting 32 is then twisted onto the Luer clearing stem connector 6. Next, the distal end wire tip 29 of the clearing member 26 is inserted a few inches into the artificial tube. The enable switch 72 is pressed to activate the reciprocating motion. While holding the artificial tube 39 in one hand, the clearing stem 26 is held in the other hand while the clearing stem 26 is advanced into the artificial tube. When the clog is initially encountered, the clearing status indicator 75 changes to alert to the initial contact, and the operator begins to apply a slight force to the clearing stem 26. Facilitating clog clearance can be achieved by the operator moving the clearing stem 26 back and forth slightly to clear the clog. These steps are repeated until the clog has cleared, in which case, the clearing status indicator 75 showing that the clog has been cleared activates. If the clog is cleared before the predetermined period (e.g., 4-20 minutes) is reached, the operator can depress the enable switch 72 again to stop the reciprocating movement and then depress the power switch 2 to shut off power to the device TCI. The clearing stem 26 can then be removed from the artificial tube (e.g., feeding tube FT) and then the working end of the clearing stem 26 can be inserted into the packaging. The artificial tube should be flushed with water to verify that the clog has been cleared; if not, the working end of the clearing stem 26 should be removed from the packaging and the clearing procedure repeated. If the clog is verified as being cleared, the clearing stem 26 is disengaged from the control box 1 in accordance with the version of the control box 1 being used. For example, if the preferred control box 1 (e.g., FIG. 16C) is being used, the alternate clearing stem fitting 32A is disengaged from the sheath attachment bracket 83 and the alternate clearing stem magnet 33A is pulled away from the alternate diaphragm 9A; alternatively, where the Luer fitting version of the control box 1 (e.g., FIG. 16A) is used, the operator twists the Luer clearing stem fitting 32 and removes the clearing stem magnet 33 end of the clearing stem 26 from the control box 1. In either situation, the clearing stem 26 is placed back in the packaging and this is discarded in a suitable biohazard container.

Figure 29:
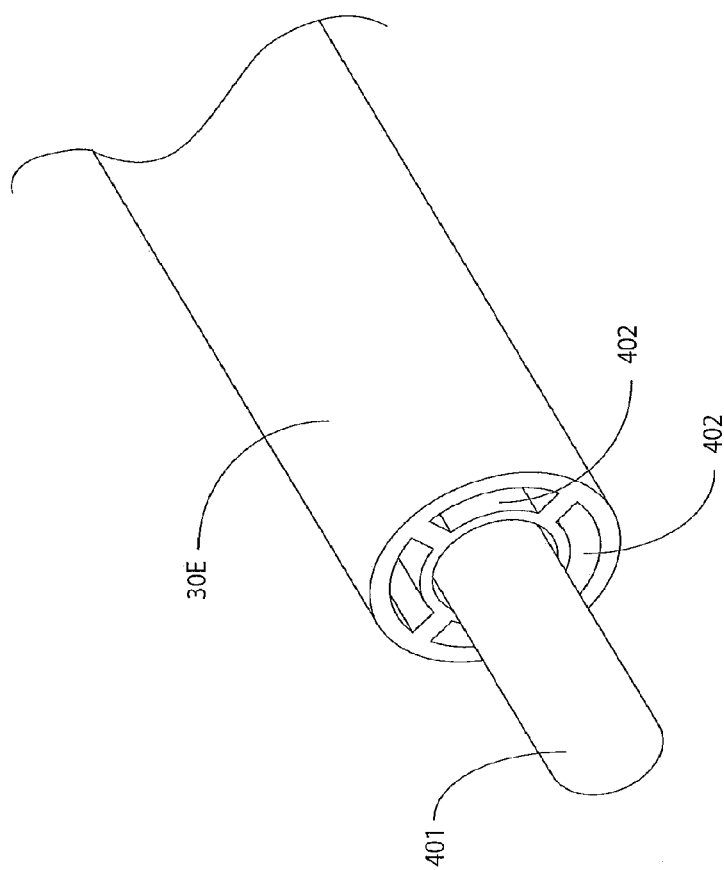
FIG. 29 is a partial isometric view of the distal end of the sheath of the tube clearers TCI and TC2 showing aspiration/irrigation ports.

FIG. 29 provides a partial isometric end view of a working end 401 of the wire 28 of the clearing stem 26 which utilizes a sheath with channels 30E that includes ports 402 which can be used for irrigation and/or aspiration. These ports 402 form the end of conduits in the sheath with channels 30E whose other ends are coupled to an aspiration source (not shown, e.g., a vacuum source, etc.) and/or an irrigation source (also not shown, e.g., a saline solution source, or other liquid source). During clog break-up, broken pieces of the clog can be aspirated out of the artificial tube using the sheath with channels 30E and where irrigating the clog vicinity is required, the sheath with channels 30E can be used to deliver such liquids. When aspirating and irrigating simultaneously, aspiration flow should equal irrigation flow rate. The appropriate flow rates are preferably 1-15 mL/min.

Another alternate clearing stem configuration is replacing the wire 28 with a hollow lumen or wire 403 to allow aspiration or irrigation down the hollow lumen or wire 403 to achieve the same purposes discussed with regard to FIG. 29. This alternative configuration is shown in FIG. 29B. Thus, the sheath ports 402 and the hollow lumen or wire 403 may cooperate in different configurations to achieve irrigation/aspiration alternatively or simultaneously. By way of example, the sheath ports 402 can be irrigating while the hollow lumen or wire 403 is suctioning, or vice versa. Alternatively, all of the ports 402 and the hollow lumen or wire 403 can be operating as irrigators or aspiration.

Figure 29A:
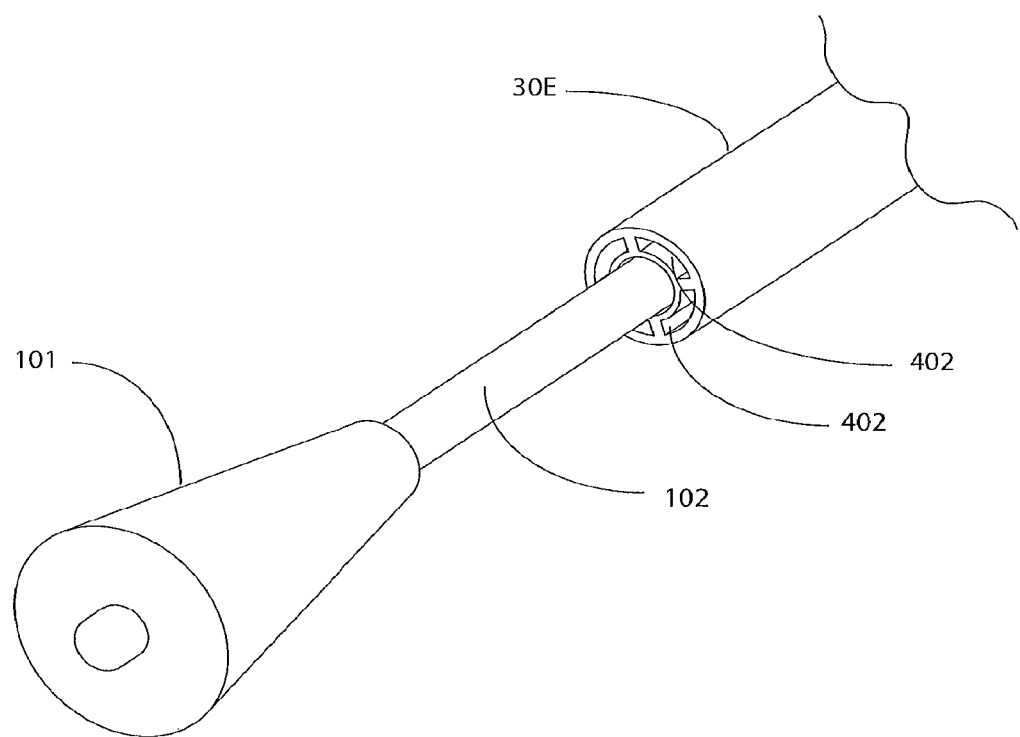
FIG. 29A is a partial isometric view of the distal end of the sheath of the tube clearers TCI and TC2 showing aspiration/irrigation ports.
Figure 29B:
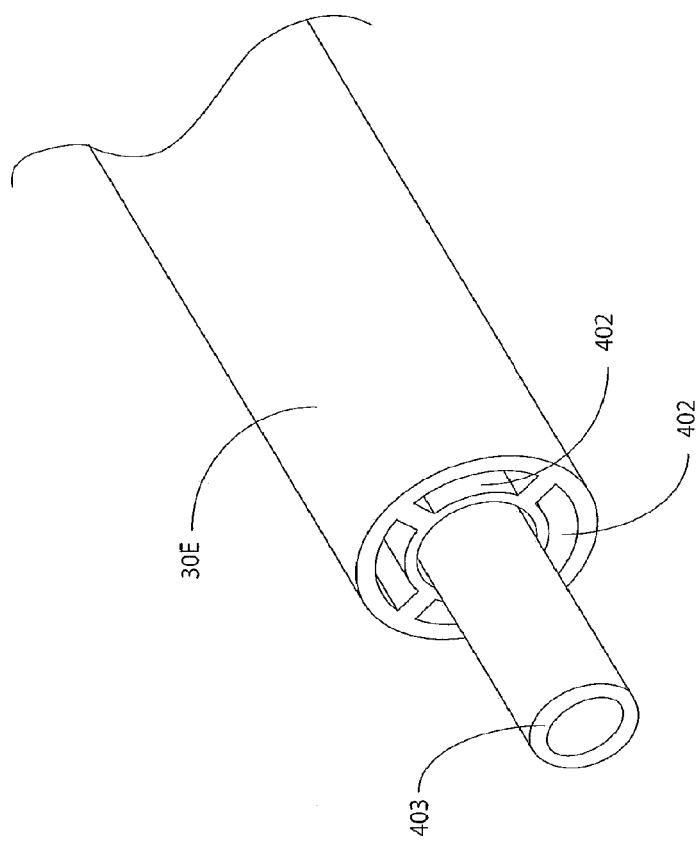
FIG. 29B is a partial isometric view of the distal end of the sheath showing a lumen or wire that is hollow.
Figure 29C:
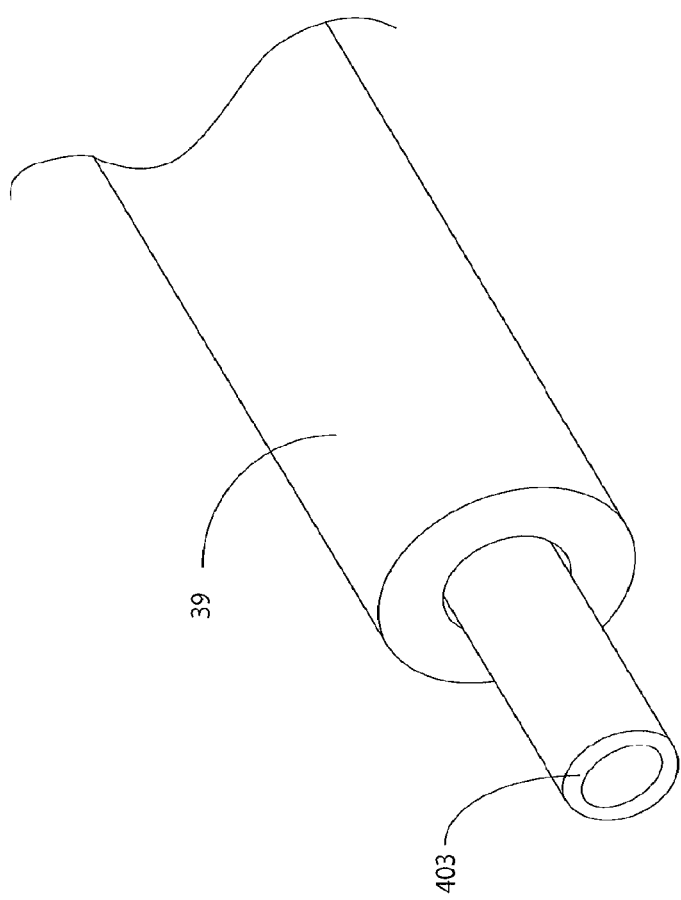
FIG. 29C is a partial isometric view of the clearing stem using only a hollow lumen or a wire only, without a sheath, effectively using the indwelling lumen as the sheath.

Another alternate clearing stem configuration is to use the indwelling artificial tube 39 effectively as the sheath, as illustrated in FIG. 29C. In this case, a wire 28 or hollow lumen or wire 403 is inserted directly into an artificial tube 39 without the sheath 30. The motor 14 drives the wire 28 or hollow lumen or wire 403 with motion as described previously, to disrupt the clog 40. Although not shown, the tube depth-control collar 22 may also be secured at the desired length to prevent over-insertion of the wire 28 or hollow lumen or wire 403, with the collar 22 impacting the end of open proximal end of the artificial tube 39 during operation. Alternatively, the wire 28 or hollow lumen or wire 403 may include the fixed tube depth-control collar 22A to also limit over-insertion. Using this configuration, the hollow lumen or wire 403 can achieve irrigation or suction alternatively. An advantage of this configuration is that elimination of the sheath can allow access to narrower lumens. The phrase "completely exposed" when used with the device TCI means a device TCI that does not use a sheath.

Figure 29D:
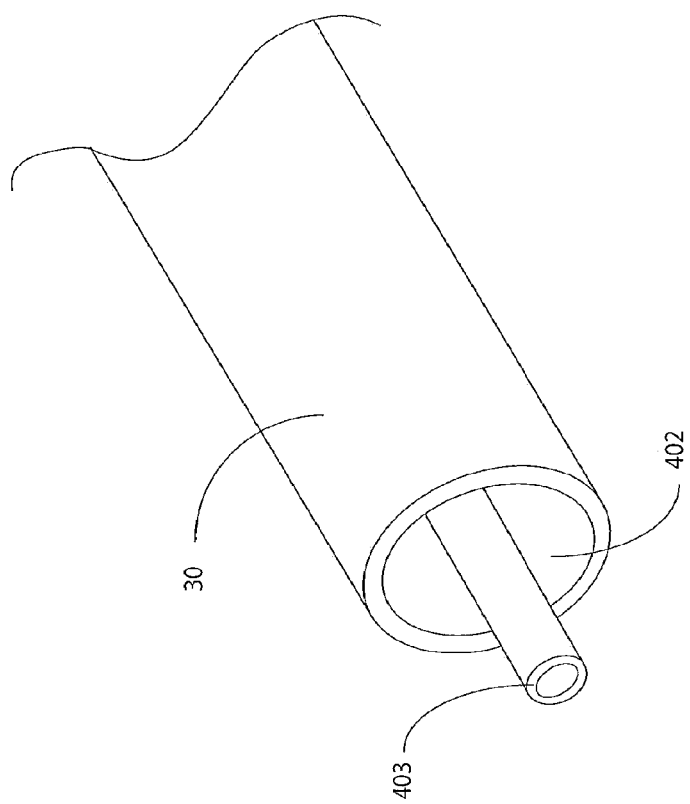
FIG. 29D is a partial isometric view of the distal end of the sheath of the tube clearers TCI and TC2 showing a very narrow hollow wire allowing aspiration/irrigation along sides of wire.

Another alternate clearing stem configuration is a very narrow hollow lumen or wire 403 compared to the sheath 30 such that the areal differential between the hollow lumen or wire 403 and sheath 30 allows for aspiration/irrigation as illustrated in FIG. 29D.

Figure 29E:
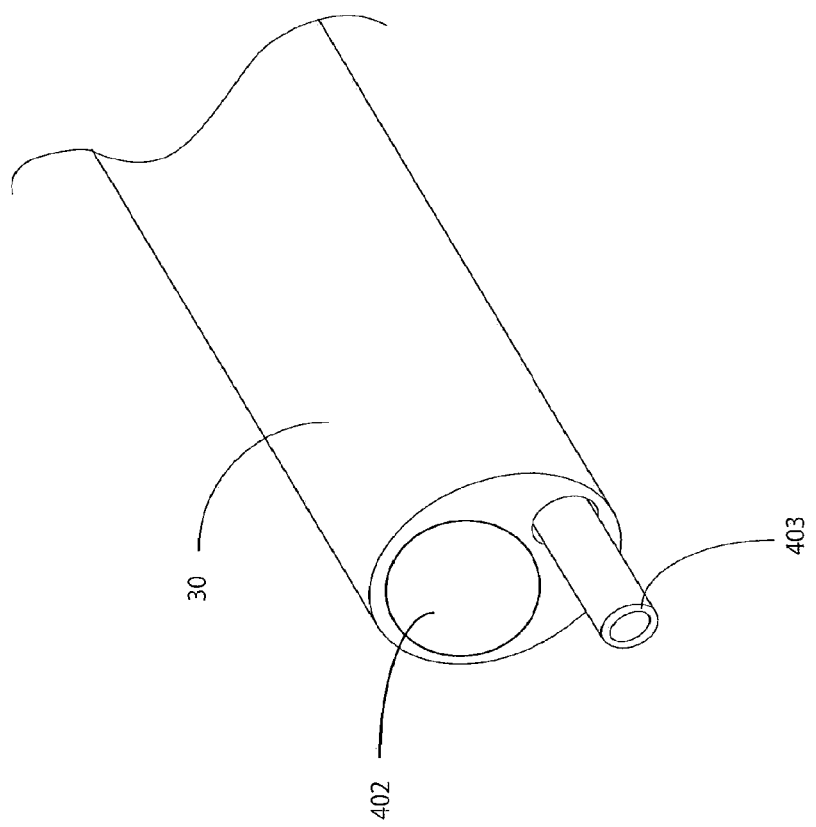
FIG. 29E is a partial isometric view of the distal end of the sheath of the tube clearers TCI and TC2 showing a small sheath channel for a very narrow hollow wire and a larger channel for aspiration/irrigation.

Another alternate clearing stem configuration is the sheath 30 has two ports. One is quite small and is possibly used for a very narrow hollow lumen or wire 403 and the port 402 is used for aspiration/irrigation as illustrated in FIG. 29E.

Rotating Tube Clearer TC2

Figure 18A:
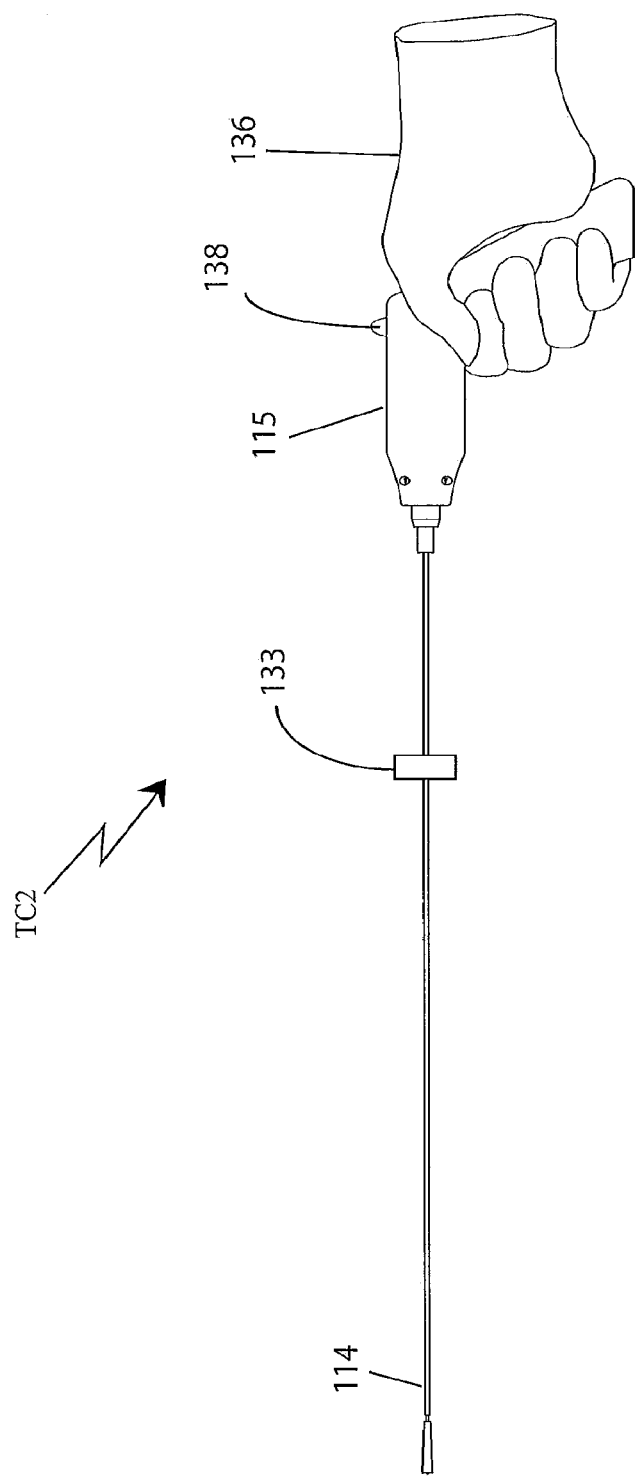
FIG. 18A depicts a hand-held version of the present invention showing the handset being gripped by the operator and including a tube depth control-collar on the clearing member.

As with TC1, tube clearer TC2 is a mechanical tube clearer but instead of generating reciprocating motion, tube clearer TC2 generates rotating motion to achieve artificial tube clearing, preferably for PEG feeding tubes. FIG. 18A depicts the tube clearer TC2 which comprises a reusable handset 115 (which remains outside the artificial tube and the patient) having a motor 108 (e.g., a DC motor) that drives (rotates) a disposable or limited-reuse clearing member 114. The handset 115 is held by the operator's hand 136 during the clearing procedure.

It should be noted that, alternatively, clearing member 114 may also be hollow for irrigation or aspiration, or other features.

The tube clearer TC2 (FIG. 19) comprises a clearing member 114 that includes a magnetic connector 103 at one end which attaches to a torque limiter 105 of the handset 115. Attached at the distal end of the clearing member 114 is a narrow flexible rod, preferably a polymer piece of tubing with a clearing brush 101 located on its distal end. The clearing member 114 can be solid or hollow. In the solid embodiment, the distal end of the clearing member 114 is attached to the clearing brush 101 and the proximal end of the clearing member 114 is attached to a magnetic connector 103. In the hollow embodiment, the wire holding the clearing brush 101 may extend the central length of the clearing member 114 to the magnetic connector 103. The clearing member 114 is flexible in order to conform to various radius of curvatures R. It is rotated by the motor 108 within the handset 115. The rotary motion of the clearing brush 101 clears the clog, occlusion, or debris from the tube (not shown).

Clearing Member and Connectors

Figure 19:
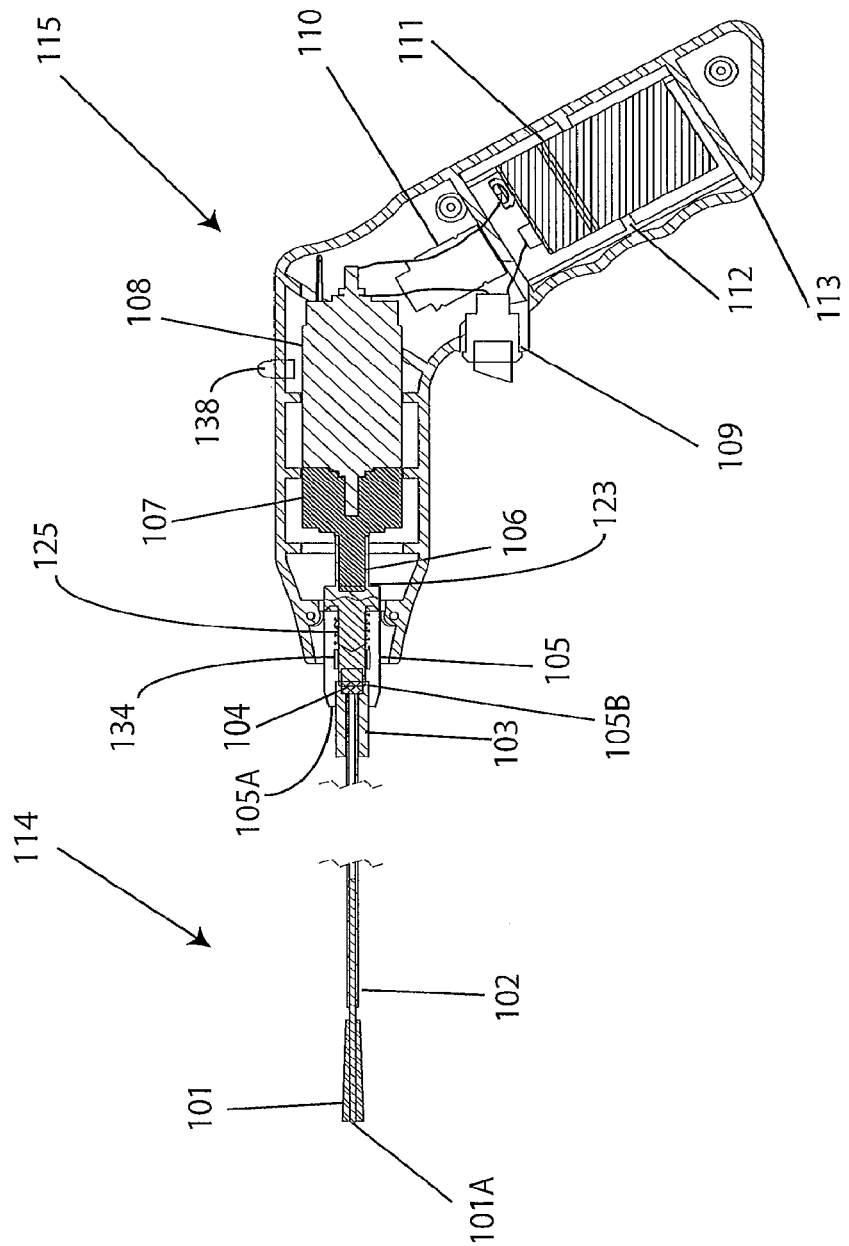
FIG. 19 is a cross-sectional view of the hand-held version of FIG. 18A.
Figure 22:
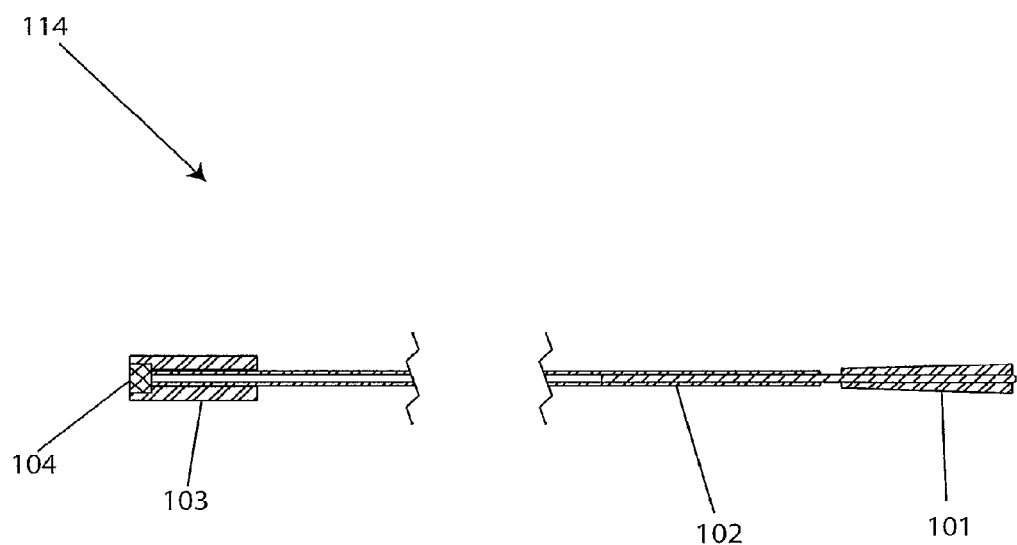
FIG. 22 is an enlarged cross-sectional view of the clearing member and its components.

The clearing member 114 comprises a polymer tube with a clearing brush 101 inset at its distal end. The preferred polymer materials are nylon and polyurethane, although other materials may be used, such as polytetrafluoroethylene (PTFE), Polyvinyl chloride (PVC), polyethylene, polypropylene, and fluoropolymer. The length of the clearing member 114 is equal to the length of the feeding tube +/− one inch, depending on application. FIG. 22 shows the layout of the clearing member 114. At the proximal end of the clearing member 114 is a polymer magnetic connector 103 which includes a clearing member magnet adapter 104 in its inner bore and which sits flush to the proximal end of the clearing member 114. To attach the clearing member 114 to the handset, as shown in FIG. 19, the magnetic connector 103 is inserted into a receiving bore 105A within the torque limiter 105 of the handset 115. Disposed within the bore end is a magnetic element 105B and wherein when the magnetic connector 103 is inserted into the receiving bore 105A, the clearing member magnet adapter 104 and magnetic element 105B contact. To facilitate a tight connection, the magnetic connector 103 comprises a hexagonal-shape, or other non-round shape, that fits into a correspondingly-shaped receiving bore 105A. DC motor 108 output is conveyed to the clearing member stem 102 through a gear train 107 and gear train output shaft 106.

Figure 23:
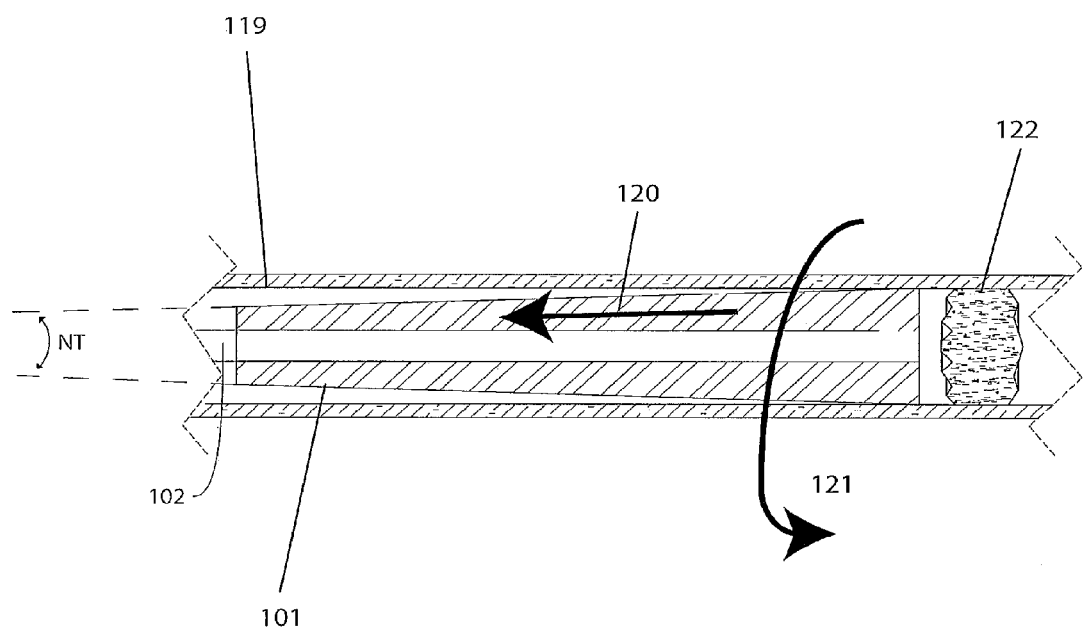
FIG. 23 is an enlarged cross-sectional view of the distal end of the clearing member which uses a helical design.

The clearing brush 101 at the distal end has several unique features. It could be a twisted-in-wire type clearing brush 101 with a negative taper NT, as shown in FIG. 23. By way of example only, the clearing brush 101 may comprise a twisted-in wire type; alternatively, the brush 101 may comprise a helical-wound wire or other type brush design. "Negative taper" implies that the dealing brush 101 bristles are wider in diameter at the distal end than at the proximal end of the clearing brush 101. There are several reasons for this configuration in the clearing member's 114 design. Most conventional brushes have a taper smaller at the distal end and larger at the proximal end. However, for this application it would require over-insertion to clear the full bore of the end of the artificial tube (e.g., feeding tube) 119. The negative taper NT also allows the helix-type wound clearing brush 101 to be extended rearward, as shown by the path of freed clog particles arrow 120 in FIG. 23. When rotating (indicated by the rotation of brush arrow 121), this clearing brush 101 design forces wicking of the loosened clog debris away from the clog 122 also in the direction of the path of freed clog particles arrow 120. This is important for fast, effective clearing. If the clog 122 was not removed from the clog site, it could be compacted further, making the clog 122 even more difficult to remove. The negative taper NT also allows for contact with the tube walls (in order to clean them), but only in a limited area. Having contact only in a limited area reduces the amount of drag on the artificial tube 119 and the torque transmitted to it and thus this minimizes any chance of dislodging the artificial tube 119 from within the patient when the clearing member 114 is removed from the artificial tube 119. The shape of the (distal) tip of the clearing brush 101 is also important for this application. Unlike many standard twisted-in-wire brushes, which are cut at the ends after twisting, the TC2 clearing brush 101 could possibly be wound with a rounded tip—the wire bends 180 degrees. This bend prevents any sharp end from coming into contact with the stomach, intestine, or other organs/tissues if over-inserted past the end of the artificial tube 119. Thus, the clearing brush 101 transfers minimal torque due to its unique geometry, but its helical design is also able to remove loosened debris from the clog 122.

In another embodiment, the brush tip 101A (FIG. 19) radius of the clearing brush 101 can be modified, e.g., rounded to allow the clearing brush 101 to break up a clog, but to not penetrate an organ (e.g., stomach or other tissue/organ, etc.) should the brush tip 101A ever make its way close to an organ. The clearing brush 101 may also be retracted from the distal end of the clearing member to decrease the chance of the clearing brush 101 catching in stomach or other tissue. In another embodiment, the brush tip 101A can be modified by the addition of a flexible tip such as a Tecoflex® tip. In another embodiment, brush tip 101A can be modified by the addition of ball tip 34E as illustrated in FIG. 5D.

Handset 115

Preferably, the handset 115 is shaped like a pistol, with contours to fit the user's fingers comfortably while he/she is using it, as shown by the operator's hand 136 (FIG. 18A). An index finger trigger 109 controls operation. The trigger 109 is a momentary power switch that only provides power when being pressed. The handset 115 is composed of three parts, one battery cover and two halves which are fastened together by screws or built-in snap fit connectors to form a handset housing 113. It also contains an isolated battery compartment 112 to facilitate battery 111 changes without exposing any components to contaminants that could cause device failure or reduce reliability. A control circuit 110 (FIG. 19) conveys power to the DC motor 108.

In this embodiment the handset contains an isolated compartment in which a common battery size is used. For example, the handset 115 can be designed to accommodate any battery size such as 9V, AA, AAA, or a specialty size and a plurality of batteries where required. Alternatively, the handset 115 may comprise a rechargeable battery such that there is no need to remove any batteries. A charger (not shown) may accompany the handset 115 such that the rechargeable battery can be inductively charged and this configuration has advantages over the battery operated setup, including: no panels are removable on the handset 115 which eliminates the possibility of contamination; and also reduces cost and disposal of batteries. The inductive charger may comprise a base unit, rechargeable battery, and circuitry. The base unit may comprise an enclosure with a slot or depression or cradle into which the handset 115 is positioned. The base unit plugs into a standard 120V outlet. A coil in the base unit transmits a magnetic field to a coil in the handset 115, and a charging circuit would transform the signal to the correct voltage and route it to the rechargeable battery located in the handset 115.

Motor

Figure 20:
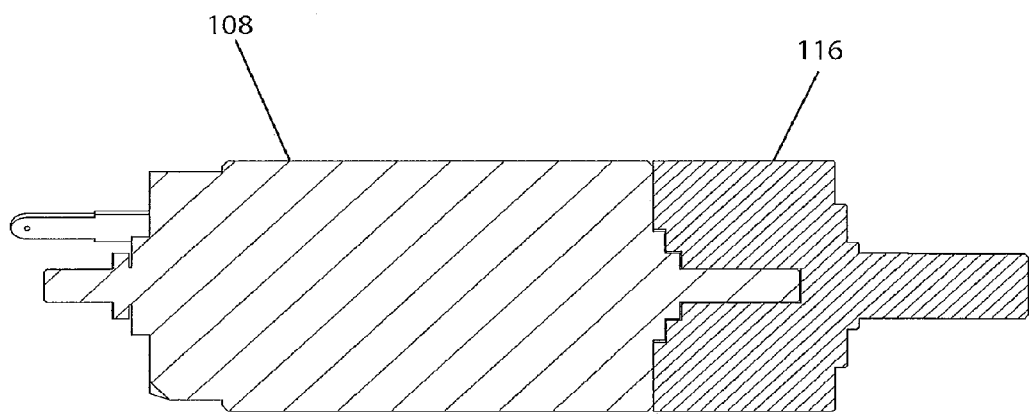
FIG. 20 is a cross-sectional view of the DC motor using a planetary gear train configuration.
Figure 21:
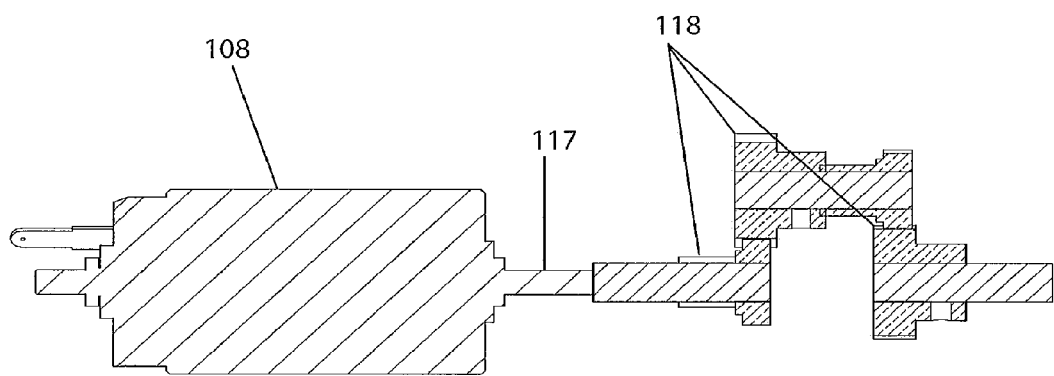
FIG. 21 is a cross-sectional view of the DC motor using a compound gear train configuration.

The motor 108 of the tube clearer TC2 is preferably a DC motor or a brushless DC motor and gear combination. The gear mechanism may be a precision gear head, such as one utilizing a planetary gear train 116 or a compound gear train 118 utilizing two or more standalone gears. Motor and gear output speed ranges from 600 RPM to 1800 RPM, more preferably 740 to 1140 RPM. The torque limiter 105 is also preferred in this embodiment. The maximum output torque can preferably range from 20 mNm to 40 mNm with a more preferable torque of 24 to 34 mNm. A voltage of less than or equal to 9 volts DC is preferred to drive the motor 108, such that standard commercially-available batteries can be used. FIG. 20 shows a DC motor 108 with a planetary gear train 116 whereas FIG. 21 shows a DC motor 108 with a compound gear train 118 configuration that is coupled to the motor output shaft 117. Thus, torque, speed and geometry of the clearing stem define the optimal operation of the device TC2. Alternatively, the motor 118 itself may have a torque output of preferably 20 mNm to 40 mNm, with a more preferable torque of 24 to 34 mNm, in which case the torque limiter 105 would not be necessary.

In another embodiment, a DC or brushless DC motor 108 and gear combination is used in combination with a torque limiter 105. The torque limiter 105 is attached in-line with the motor output shaft 117 and allows slippage once the maximum output torque is reached. In another embodiment, a DC or brushless DC motor 108 and gear combination is used in combination with a hammering device, similar to that found in hammer drills (U.S. Pat. No. 5,653,294 (Thurler, et al.) and whose entire disclosure is incorporated by reference herein). This device creates an oscillatory motion along with the rotary motion to clear the clog. In another embodiment, the DC or brushless DC motor in all examples above is replaced with a piezoelectric motor with similar specifications.

Tube Depth-Control Collar

Figure 24:
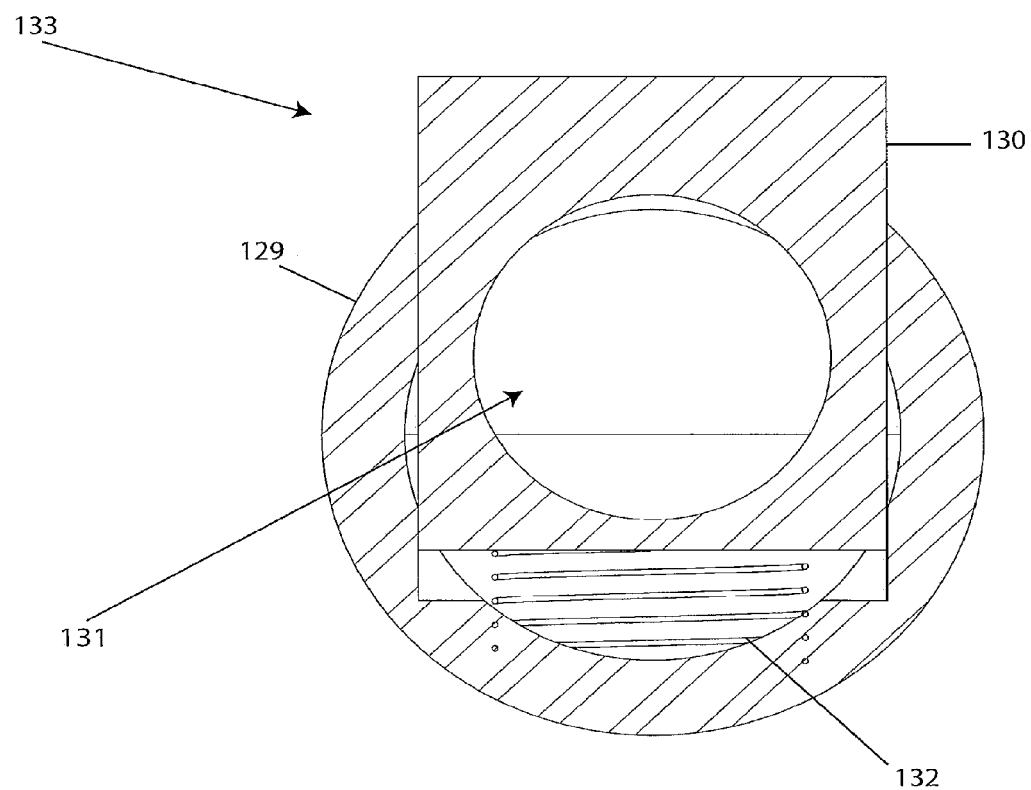
FIG. 24 is an enlarged cross-sectional view of the push-button actuated tube depth-control collar.

As with TCI, tube clearer TC2 comprises a tube depth-control collar 133, as shown in FIG. 24. This depth-control collar permits one-handed operation using no special tools. The tube depth-control collar 133 mounts along the rod portion of the clearing member 114. The tube depth-control collar 133 is formed to be well-balanced and lightweight so as to not cause unwanted harmonics in the clearing member 114 during rotation. The tube depth-control collar 133 comprises a lightweight, circular tube depth-control collar housing 129 which includes a displaceable tube depth-control collar push button 130 that acts against a preloaded spring 132 bias and which locks against the clearing member 114 which passes through the opening for clearing member 131. FIG. 18A depicts the tube depth-control collar 133 on the clearing member 114.

Motor Torque Limiting

Figure 25:
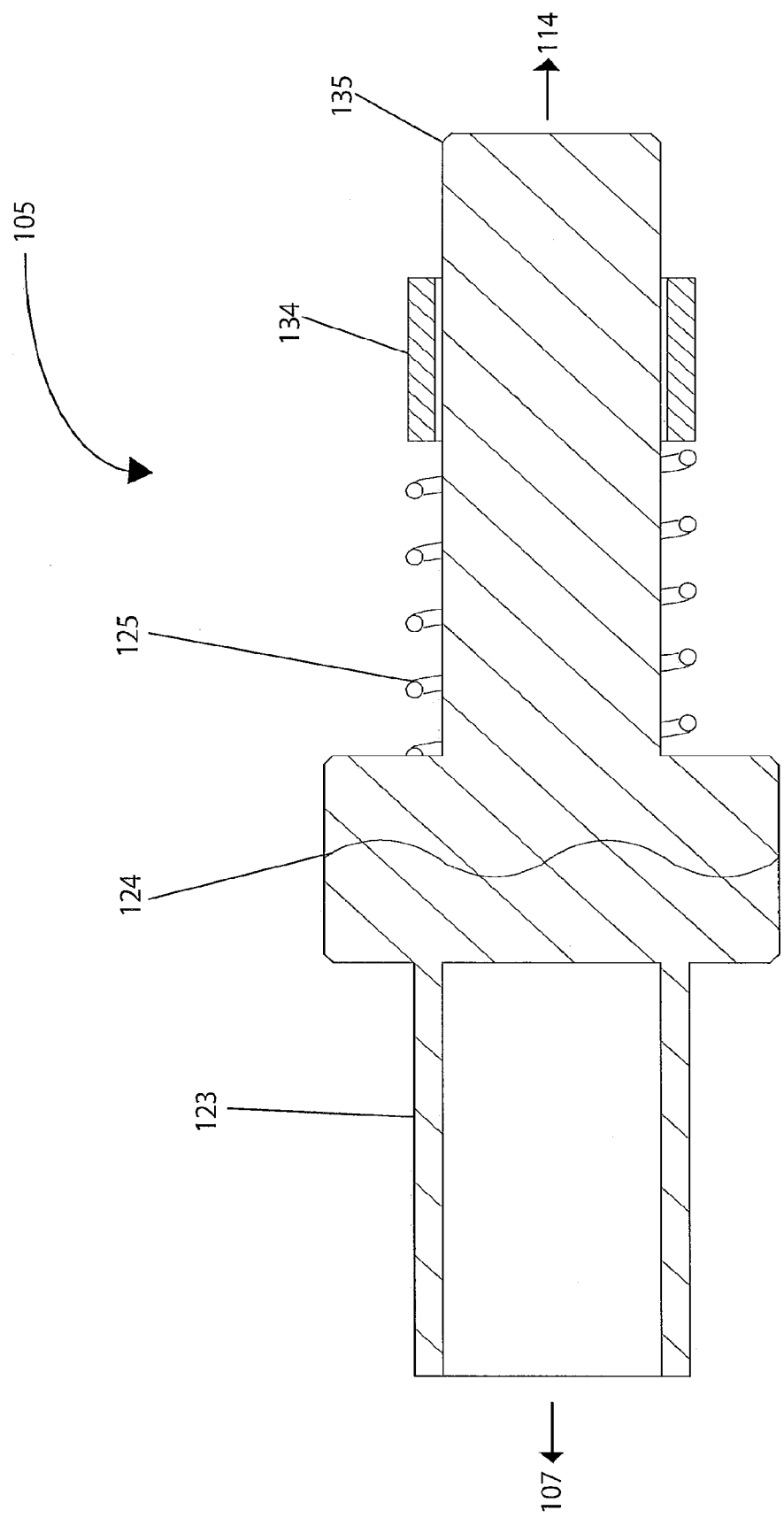
FIG. 25 is an enlarged cross-sectional view of a torque-limiter that is designed to slip once a certain applied torque is exceeded.

In a preferred embodiment of the handset 115, the torque applied to the clearing member 114 is limited by controlling the voltage and current applied to the DC motor and ultimately to the gears. These voltage and current limits are established by testing and determining the minimum angle of twist that are unacceptable when the clearing brush 101 is in a locked condition within tubes under test. An alternative method involves the use of a DC motor with a torque limiter 105 as depicted in FIGS. 19 and 25. The torque limiter 105 is a two-piece patterned disc, preloaded by a preload spring 125. The spring force controls torque at which disc slippage occurs. In particular, the torque limiter 105 comprises an input coupler 123, a torque limiter output shaft 135, a preload collar 134 and a torque limiter profile 124. The input coupler 123 couples to the gear train 107 and the torque limiter output shaft 135 couples the clearing member 114. As can be appreciated, when a certain applied torque is exceeded, the torque limiter 105 is designed to slip at the interface or torque limiter profile 124 to disengage and thereby prevent the clearing member 114 from exceeding the torque limit.

Clearing Member Control

Figure 26:
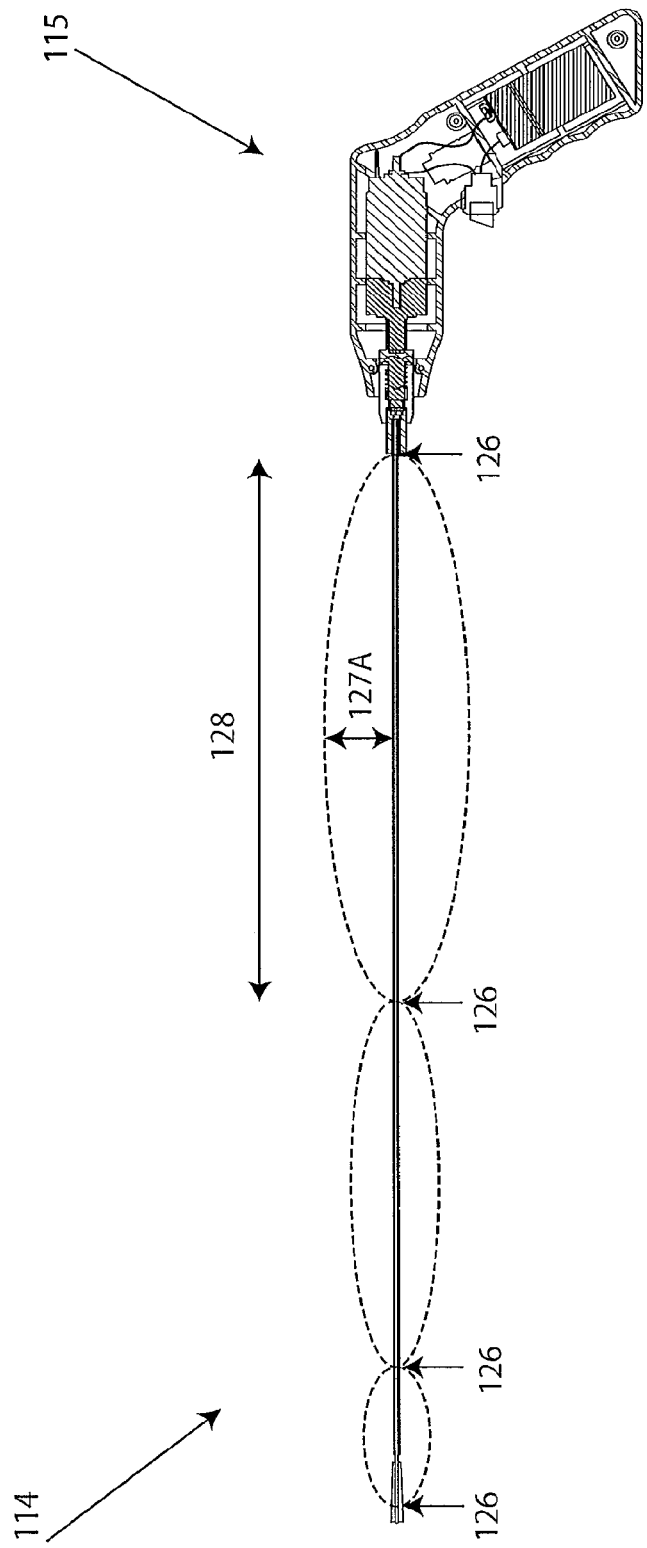
FIG. 26 is a cross-sectional view of the hand-held version of the present invention depicting the multi-nodal harmonics while the clearing member is spinning.
Figure 27:
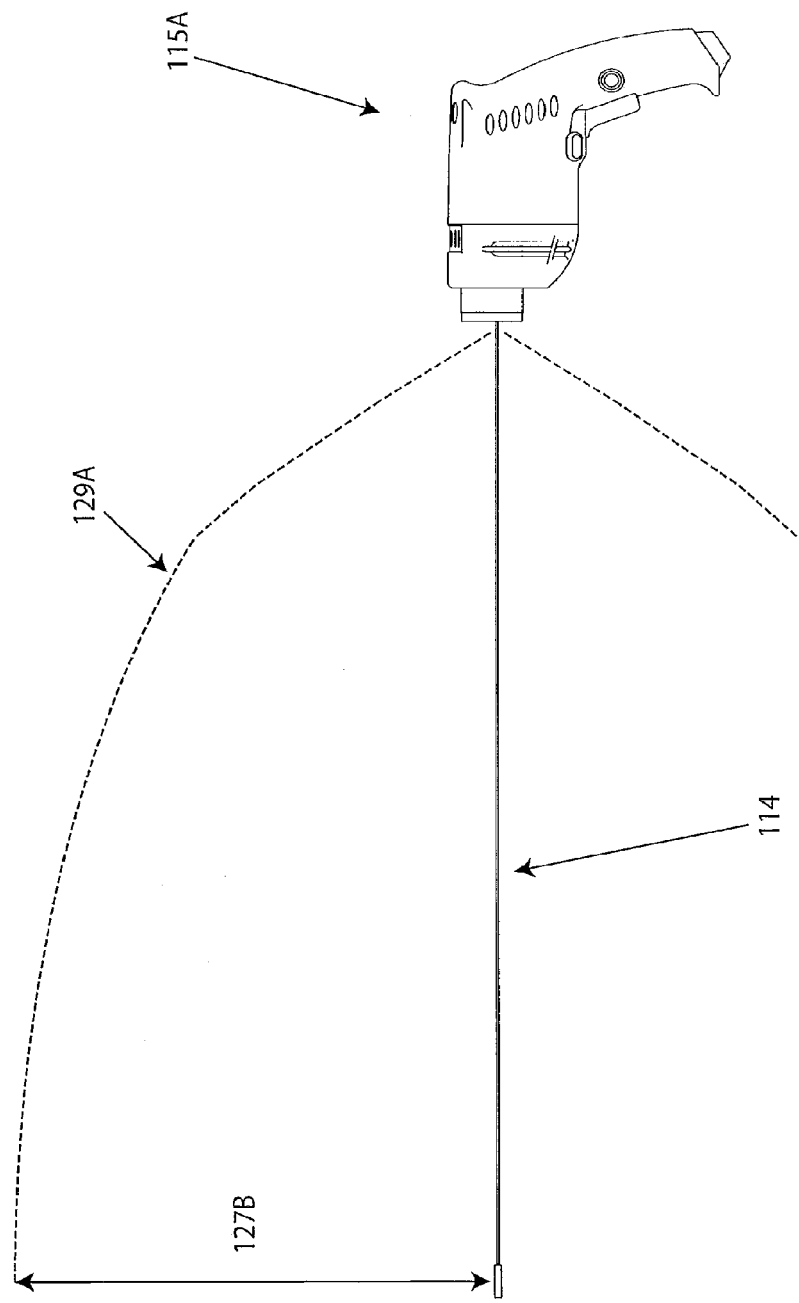
FIG. 27 is a cross-sectional view of a prior-art hand-held device that generates rotatable motion depicting undesired operation with only a nodal point at the proximal end of the clearing stem.

The tube clearer TC2 must control harmonics so that the clearing member 114 does not become uncontrollable and cause injury/damage. During device activation, the tube clearer TC2 rotates the clearing member 114 with a displacement diameter that is preferably from 0 mm to 40 mm and a more preferred diameter of 25.4 mm or less. FIG. 26 shows multi-nodal harmonics (i.e., node points 126) occurring in the clearing member 114 while spinning and also depicts the maximum desired displacement 127A. This is preferred as its shape limits the displacement by geometry. The distance between the first two nodal points 126 is indicated by distance between nodal points 128, and as can be seen in FIG. 26, this distance decreases for subsequent nodal points 126. The maximum desired displacement 127A of the clearing stem is preferred to be kept to 25.4 mm or less. In contrast, FIG. 27 depicts a commercially-available rotary tool 115A (e.g., a hand-held drill) rotating the clearing member 114, showing the undesirable profile of rotating stem 129A (and its undesirable corresponding maximum radial displacement 127B) of the clearing stem motion because there is only one nodal point at the proximal end of the clearing member 114. This type of deformation is not preferred because it is more likely to be unstable.

Figure 28:
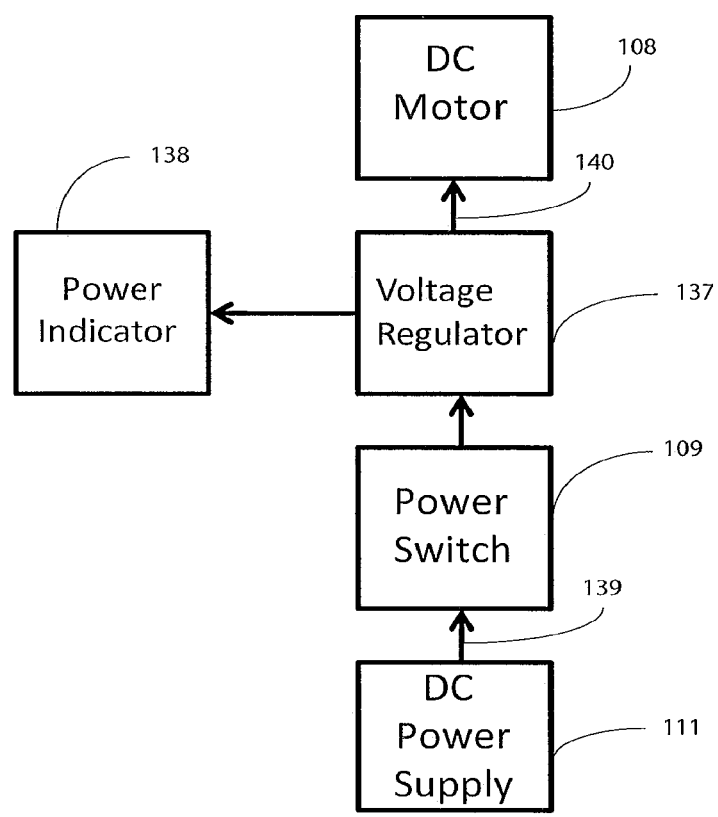
FIG. 28 is a block diagram of the control box electronics for the rotating tube clearer (TC2) configuration.

FIG. 28 depicts a block diagram of the electronics of the device TC2. In particular, a DC motor 108 provides the rotational motion to the clearing stem 114. The motor 108 receives its input voltage 140 from a voltage regulator 137 which in turn receives power 139 from a power source or battery 111 (e.g., 9V battery, a rechargeable battery, etc.) when the trigger 109 is activated by the operator. A power indicator 138 (see FIG. 18A also), driven by the voltage regulator, is also provided.

FIG. 29A provides a partial isometric end view of the device TC2 showing the clearing brush 101 coupled to the clearing member stem 102 which utilizes a sheath with channels 30E that includes ports 402 which can be used for irrigation and/or aspiration. These ports 402 form the end of conduits in the sheath with channels 30E whose other ends are coupled to an aspiration source (not shown, e.g., a vacuum source, etc.) and/or an irrigation source (also not shown, e.g., a saline solution source, or other liquid source). During clog break-up, broken pieces of the clog can be aspirated out of the artificial tube using the sheath with channels 30E and where irrigating the clog vicinity is required, the sheath with channels 30E can be used to deliver such liquids. When aspirating and irrigating simultaneously, aspiration flow should equal irrigation flow rate. The appropriate flow rates are preferably between 1-15 mL/min. The clearing brush 101 can also be placed back along the clearing member stem 102 away from the distal end of the clearing member 114 to decrease the potential for the clearing brush 101 grabbing or interacting with the stomach or other organ or tissue. Alternatively, the various configurations shown in FIGS. 29 and 29B-29E can also be used with the device TC2. The phrase "completely exposed" when used with the device TC2 means a device TC2 that does not use a sheath.

Figure 18B:
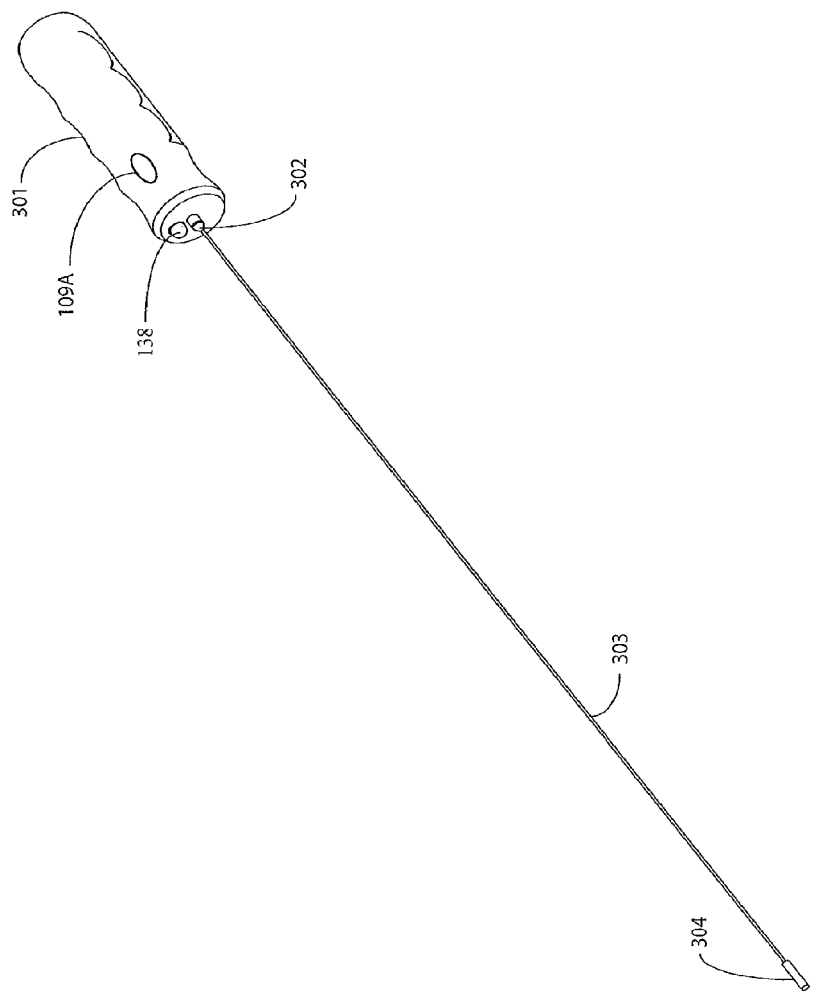
FIG. 18B depicts an alternative hand-held version of the present invention.
Figure 18C:
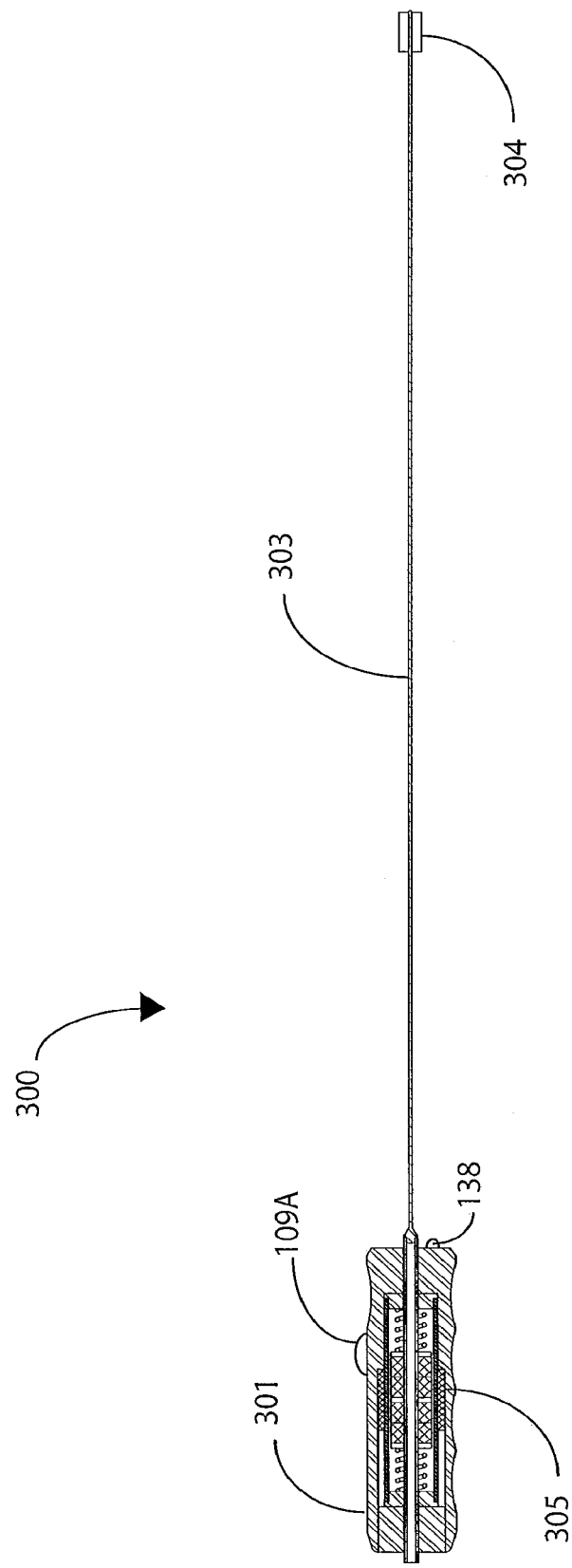
FIG. 18C is a side view of the alternative hand-held version showing the hand grip in cross-section.

FIGS. 18B-18C depict an alternative voice coil motor tube clear device TC2. Instead of using a "pistol-style" housing, the device TC2 of FIGS. 18B-18C comprise an elongated hand grip 301. In addition, unlike the rotational motion of the TC2 device shown in FIG. 18A, the alternative voice coil motor tube clear device 300 generates reciprocating motion (as discussed previously with regard to the TCI devices). In particular, within the hand grip 301 is positioned a voice coil motor 305 that, when energized, causes the clearing stem 303 to reciprocate. The tip of the clearing stem 303 includes a clearing brush 304. As shown most clearly in FIG. 18B, a clearing stem adapter 302 is provided on an end of the hand grip 301 for securing the clearing stem 303 to the voice coil motor 305 in the hand grip 301. A power indicator 138 is also provided to indicate when power is being provided to the clearing stem 303 for reciprocating motion. A power switch/trigger 109A is provided so that the user can manually control the activation of the device, similar to the pistol-style embodiment.

It should be noted that, alternatively, clearing stem 303 may also be hollow for irrigation or aspiration, or other features and may have similar configurations as shown in FIGS. 29-29E.

It should be further understood that the preferred embodiments of the present invention are for the in-situ clearing of artificial lumens in a living being, but that these embodiments can be used for clearing lumens located outside of the living being, as well as for clearing other types of lumens not associated with living beings.

Now that exemplary embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

APPENDIX

Reference Characters and Their Associations

| | | |
|---|---|---|
| APA | Amplified Piezoelectric Actuator | TCI |
| CR | Crank | TCI |
| DS | Displacement Sensor | TCI |
| IS | Impedance Sensor | TCI |
| NT | Negative Taper Angle | TC2 |
| SY | Scotch Yoke | TCI |
| SS | Soft Stop | TC1/TC2 |
| TCI | Tube Clearing Device 1 | TCI |
| TC2 | Tube Clearing Device 2 | TC2 |
| TCS | Tip Compression Spring | TCI |
| GL | Green Light | TCI |
| YL | Yellow Light | TCI |
| FT | Artificial/Feeding Tube | TC1/TC2 |
| R | Radius of Curvature | TCI |
| 1 | Control Box | TCI |
| 2 | Power Switch | TCI |
| 3 | Power Indicator | TCI |
| 4 | Fault Indicator | TCI |
| 5 | Power Plug | TCI |

APPENDIX-continued

Reference Characters and Their Associations

| | | |
|---|---|---|
| 6 | Clearing Stem Connector | TCI |
| 7 | Motor Mount | TCI |
| 8 | Motor Mount Damper | TCI |
| 9 | Diaphragm | TCI |
| 9A | Alternate Diaphragm | TCI |
| 10 | Electronics | TCI |
| 11 | Motor PCB | TCI |
| 12 | Magnet | TCI |
| 12A | Magnet Recess | TCI |
| 13 | Motor Magnetic Coupler | TCI |
| 13A | Alternate Motor Magnetic Coupler | TCI |
| 14 | Motor | TCI |
| 14A | Counter Balance Mechanism | TCI |
| 15 | Motor Shaft | TCI |
| 16 | VCM Body | TCI |
| 17 | Winding | TCI |
| 18 | End Bearing | TCI |
| 19 | Spring | TCI |
| 20 | Magnets | TCI |
| 20N-20S | Magnetic Driving members | TCI |
| 21A-21C | Pole Pieces | TCI |
| 22 | Tube Depth-Control collar | TCI |
| 22A | Fixed Tube Depth-Control collar | TCI |
| 23 | Depth Control Collar Push Button | TCI |
| 23A | Central passageway of push button | TCI |
| 23B | Lower portion of press button | TCI |
| 24 | Tube Depth-Control Collar Body | TCI |
| 24A | Central passageway of collar body | TCI |
| 24B | Upper portion of collar body | TCI |
| 25 | Spring | TCI |
| 26 | Clearing Stem | TCI |
| 27 | Wire Stop | TCI |
| 27A | Alternate Wire Stop | TCI |
| 28 | Wire | TCI |
| 28A | Wire Protrusion | TCI |
| 29 | Wire Tip | TCI |
| 30 | Sheath | TCI |
| 30A | Sheath length markings | TCI |
| 30B | Integer markings | TCI |
| 30C | Distal End | TCI |
| 30D | Proximal End | TCI |
| 30E | Sheath with Channels | TCI |
| 31 | Stem Stiffener | TCI |
| 32 | Clearing Stem Fitting | TCI |
| 32A | Alternate Clearing Stem Fitting | TCI |
| 33 | Clearing Stem Magnet | TCI |
| 33A | Alternate Clearing Stem Magnet | TCI |
| 33B | Alternate Clearing Stem Magnet Fitting | TCI |
| 34 | Plastic Wire Tip | TCI |
| 34A | Alternate Tubing Tip | TC1/TC2 |
| 34B | Fixed Member | TC1/TC2 |
| 34C | Gripping/Chopping Mechanism | TCI |
| 34D | Pivot Point | TCI |
| 34E | Ball Tip | TC1/TC2 |
| 35 | Wire Tip Brush | TCI |
| 36 | Sheath Tip Brush | TCI |
| 37 | Forward Swept Sheath Tip Brush | TCI |
| 38 | Nursing Cart | TCI |
| 38A | Pole | TCI |
| 39 | Artificial Tube | TCI |
| 40 | Clog | TCI |
| 41 | Tube Inner Lumen | TCI |
| 42 | Pneumatic Motor | TCI |
| 43 | Pneumatic Motor Housing | TCI |
| 44 | Pneumatic Motor Shaft | TCI |
| 46 | Pneumatic Motor Diaphragm | TCI |
| 47 | Internal Tubing | TCI |
| 48 | Scotch Yoke Motor | TCI |
| 49 | DC Motor | TCI |
| 50 | Scotch Yoke Slider | TCI |
| 50A | Scotch Yoke Forward Displacement direction | TCI |
| 50B | Scotch Yoke Rearward Displacement direction | TCI |
| 51 | Adapter | TCI |
| 52 | Scotch Yoke Shaft | TCI |
| 53 | Wires | TCI |
| 54 | Air Supply Inlet | TCI |

APPENDIX-continued

Reference Characters and Their Associations

| | | |
|---|---|---|
| 55 | Solenoid Motor | TC1 |
| 56 | Solenoid | TC1 |
| 57 | Solenoid Shaft | TC1 |
| 58 | Return Spring | TC1 |
| 59 | APA Motor | TC1 |
| 60 | Actuator | TC1 |
| 61 | Actuator Mount | TC1 |
| 62 | Actuator Shaft | TC1 |
| 63 | Electronic System | TC1 |
| 66 | Fuse | TC1 |
| 67 | Power | TC1 |
| 69 | Micro Processor Power Unit (MPU) | TC1 |
| 70 | +3.3 VDC | TC1 |
| 71 | Microprocessor | TC1 |
| 72 | Enable Switch | TC1 |
| 73 | Power Electronics | TC1 |
| 75 | Clearing Status Indicator | TC1 |
| 75A | Indicator | TC1 |
| 76 | power signal to motor | TC1 |
| 77 | Langevin Transducer motor | TC1 |
| 78 | Piezoelectric elements | TC1 |
| 79 | Pre-stress bolt | TC1 |
| 80 | Tail Mass | TC1 |
| 81 | Horn | TC1 |
| 82 | Clearing Stem Attachment | TC1 |
| 83 | Sheath Attachment Bracket | TC1 |
| 84 | Diaphragm Sealing Ring | TC1 |
| 85 | Power Up | TC1 |
| 86 | Initialization | TC1 |
| 87 | Disabled | TC1 |
| 88 | Enabled | TC1 |
| 89 | Enable Button Pressed | TC1 |
| 90 | Fault Detected | TC1 |
| 91 | Fault | TC1 |
| 92 | Power Cycle | TC1 |
| 93 | Time Interval | TC1 |
| 101 | Clearing Brush | TC2 |
| 101A | Brush tip | TC2 |
| 102 | Clearing Member Stem | TC2 |
| 103 | Magnetic Connector | TC2 |
| 104 | Magnetic Adapter | TC2 |
| 105 | Torque Limiter | TC2 |
| 105 A | Receiving Bore | TC2 |
| 105B | Magnetic Element | TC2 |
| 106 | Gear Train Output Shaft | TC2 |
| 107 | Gear Train | TC2 |
| 108 | Motor | TC2 |
| 109 | Trigger | TC2 |
| 109A | Power Switch/trigger | TC2 |
| 110 | Control Circuit | TC2 |
| 111 | Battery | TC2 |
| 112 | Battery Compartment | TC2 |
| 113 | Handset Housing | TC2 |
| 114 | Clearing Member | TC2 |
| 115 | Handset | TC2 |
| 115A | Commercial Available Rotary Tool | TC2 |
| 116 | Planetary Gear Train | TC2 |
| 117 | Motor Output Shaft | TC2 |
| 118 | Compound Gear Train | TC2 |
| 119 | Artificial Tube | TC2 |
| 120 | Path of Freed Clog Particles | TC2 |
| 121 | Rotation of Brush Arrow | TC2 |
| 122 | Clog | TC2 |
| 123 | Input Coupler | TC2 |
| 124 | Torque Limiter Profile | TC2 |
| 125 | Preload Springs | TC2 |
| 126 | Nodal Points | TC2 |
| 127 A | Maximum Desired Displacement | TC2 |
| 127B | Undesirable Displacement | TC2 |
| 128 | Distance between nodal points | TC2 |
| 129 | Tube depth-control collar housing | TC2 |
| 129 A | Undesired Profile of Rotating Stem | TC2 |
| 130 | Tube Depth-Control Collar Push Button | TC2 |
| 131 | Opening for Clearing Member | TC2 |
| 132 | Preloaded Spring | TC2 |
| 133 | Tube depth-control collar | TC2 |
| 134 | Preload Collar | TC2 |
| 135 | Torque Limiter Output Shaft | TC2 |

APPENDIX-continued

Reference Characters and Their Associations

| | | |
|---|---|---|
| 136 | Operator's Hand | TC2 |
| 137 | Voltage Regulator | TC2 |
| 138 | Power Indicator | TC2 |
| 139 | Power | TC2 |
| 140 | Input Voltage | TC2 |
| 300 | Voice Coil Motor (VCM) Tube Clear | TC2 |
| 301 | Hand Grip | TC2 |
| 302 | Clearing Stem Adapter | TC2 |
| 303 | Clearing Stem | TC2 |
| 304 | Clearing Brush | TC2 |
| 305 | Voice Coil Motor | TC2 |
| 401 | Working End | TC1/TC2 |
| 402 | Port | TC1/TC2 |
| 403 | Hollow Lumen or Wire | TC1/TC2 |

While the invention has been described in detail and with reference to specific examples thereof, it will be apparent to one skilled in the art that various changes and modifications can be made therein without departing from the spirit and scope thereof.

What is claimed is:

1. A device for the clearing of a blockage in an artificial tube completely or partially disposed within a living being, comprising:
   a controller having an actuator for generating repetitive motion; and
   a clearing member having a sheath located within the artificial tube, wherein the clearing member has a wire that extends through the sheath and extends out of a distal end of the sheath in a distal direction and is located within the artificial tube, wherein the actuator imparts repetitive motion to the wire to cause the wire to move in relation to the sheath such that a first portion of the wire moves into and out of the distal end of the sheath at a location within the artificial tube while a second portion of the wire distal to the first portion of the wire remains distal to and outside of the distal end of the sheath while the wire has the repetitive motion imparted thereon, wherein a wire tip of the wire engages the blockage in the artificial tube.

2. The device of claim 1 further comprising a tube depth-control collar along a length of the clearing member that engages the sheath.

3. The device of claim 2 wherein the tube depth-control collar fixed on the clearing member and does not move relative to the sheath.

4. The device of claim 2 wherein the tube depth-control collar is adjustable along the clearing member such that the position of the tube depth-control collar relative to the sheath changes.

5. The device of claim 1, wherein the wire tip is rounded in shape.

6. The device of claim 1, wherein the wire is hollow for permitting irrigation or aspiration at an end of the wire.

7. The device of claim 1, wherein the sheath has a plurality of ports that terminate at a distal end of the sheath.

8. The device of claim 1, wherein the artificial tube is a feeding tube, wherein a portion of the sheath is located inside of the feeding tube and wherein a portion of the sheath is located outside of and proximal to the feeding tube, wherein a portion of the wire is located inside of the feeding tube and wherein a portion of the wire is located outside of and proximal to the feeding tube.

9. The device of claim 1, wherein the sheath remains stationary with respect to the artificial tube and wherein the wire moves relative to the artificial tube when the actuator imparts relative motion to the wire.

10. A device, comprising:
a feeding tube;
a controller having an actuator that generates repetitive motion;
a clearing member having a sheath and a wire, wherein the wire is disposed through the sheath; and
a tube-depth control collar that engages the sheath and that engages the feeding tube;
wherein the actuator imparts repetitive motion to the wire to cause the wire to move in relation to the tube-depth control collar, and to cause the wire to move in relation to the feeding tube;
wherein the wire extends out of a distal end of the sheath in a distal direction and is located within the feeding tube, wherein the actuator imparts repetitive motion to the wire to cause the wire to move in relation to the sheath such that a of the wire moves into and out of the distal end of the sheath at a location within the feeding tube while a second portion of the wire distal to the first portion of the wire remains distal to and outside of the distal end of the sheath while the wire has the repetitive motion imparted thereon.

11. The device of claim 10 herein the wire has a wire tip that engages a blockage in the feeding tube; and
wherein the tube depth-control collar, the sheath, and the feeding tube remain stationary with respect to one another.

12. The device of claim 10 wherein the tube depth-control collar is fixed on the clearing member and does not move relative to the sheath.

13. The device of claim 10 wherein the tube depth-control collar is adjustable along the clearing member such that the position of the tube depth-control collar relative to the sheath changes.

14. The device of claim 10, wherein a portion of the sheath is located inside of the feeding tube and wherein a portion of the sheath is located outside of and proximal to the feeding tube, wherein a portion of the wire is located inside of the feeding tube and wherein a portion of the wire is located outside of and proximal to the feeding tube.

15. A device for the in situ clearing of a blockage in an artificial tube completely or partially disposed within a living being, comprising:
a controller that remains outside of the living being, the controller having an actuator for generating repetitive motion;
a clearing member having a sheath located within the artificial tube, wherein the clearing member has a wire that extends through the sheath and extends out of a distal end of the sheath in a distal direction and is located within the artificial tube, wherein the actuator imparts repetitive motion to the wire to cause the wire to move in relation to the sheath such that a first portion of the wire moves into and out of the distal end of the sheath at a location within the artificial tube while a second portion of the wire distal to the first portion of the wire remains distal to and outside of the distal end of the sheath while the wire has the repetitive motion imparted thereon, wherein a wire tip of the wire engages the blockage in the artificial tube; and
a tube-depth control collar that engages the sheath and the artificial tube, wherein the tube-depth control collar limits insertion depth of the sheath into the artificial tube, wherein the repetitive motion of the wire causes the wire to move in relation to the tube-depth control collar.

16. The device of claim 15 wherein the tube depth-control collar is fixed on the clearing member and does not move relative to the sheath and does not move relative to the artificial tube.

17. The device of claim 15 wherein the tube depth-control collar is adjustable along the clearing member such that the position of the tube depth-control collar relative to the sheath changes.

18. The device of claim 15, wherein the wire tip is rounded in shape, and wherein the artificial tube is a feeding tube.

* * * * *

UNITED STATES PATENT AND TRADEMARK OFFICE
CERTIFICATE OF CORRECTION

PATENT NO.        : 8,906,169 B2
APPLICATION NO.   : 14/052917
DATED             : December 9, 2014
INVENTOR(S)       : Roger B Bagwell et al.

It is certified that error appears in the above-identified patent and that said Letters Patent is hereby corrected as shown below:

In the Specification

In the Statement Regarding Federally Sponsored Research or Development section at column 1, line 32, the phrase "HP-0810029" should be changed to read --IIP-0810029--.

In the Claims

In claim 10 at column 29, line 21, "a of the wire" should be changed to read --a first portion of the wire--.

In claim 11 at column 29, line 27, the words "claim 10 herein" should be changed to read --claim 10, wherein--.

Signed and Sealed this
Thirtieth Day of June, 2015

Michelle K. Lee
*Director of the United States Patent and Trademark Office*